United States Patent
Shippy, III et al.

(10) Patent No.: US 8,275,455 B2
(45) Date of Patent: Sep. 25, 2012

(54) MEDICAL DEVICES EMPLOYING CONDUCTIVE POLYMERS FOR DELIVERY OF THERAPEUTIC AGENTS

(75) Inventors: James Lee Shippy, III, Wilmington, NC (US); Jan Weber, Maastricht (NL); Karl Jagger, Deephaven, MN (US); Tracee Eidenschink, Wayzata, MN (US); Liliana Atanasoska, Edina, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 12/487,203

(22) Filed: Jun. 18, 2009

(65) Prior Publication Data

US 2009/0318848 A1    Dec. 24, 2009

Related U.S. Application Data

(60) Provisional application No. 61/074,456, filed on Jun. 20, 2008.

(51) Int. Cl.
*A61N 1/30* (2006.01)

(52) U.S. Cl. ........................ 604/20; 604/890.1

(58) Field of Classification Search ........... 604/191, 604/891.1, 892.1
See application file for complete search history.

(56) References Cited

U.S. PATENT DOCUMENTS

| | | | |
|---|---|---|---|
| 4,585,652 A | 4/1986 | Miller et al. | |
| 5,733,925 A | 3/1998 | Kunz et al. | |
| 6,287,294 B1 | 9/2001 | Lemelson | |
| 6,490,483 B2 * | 12/2002 | Willis | 604/20 |
| 6,730,072 B2 * | 5/2004 | Shawgo et al. | 604/890.1 |
| 2002/0111601 A1 | 8/2002 | Thompson | |
| 2003/0099684 A1 | 5/2003 | Domb | |
| 2004/0182704 A1 | 9/2004 | Daunert et al. | |
| 2004/0248320 A1 * | 12/2004 | Santini et al. | 436/174 |
| 2006/0013850 A1 | 1/2006 | Domb | |
| 2006/0184092 A1 * | 8/2006 | Atanasoska et al. | 604/20 |
| 2007/0239256 A1 * | 10/2007 | Weber et al. | 623/1.15 |
| 2008/0097280 A1 | 4/2008 | Martin et al. | |

FOREIGN PATENT DOCUMENTS

| | | |
|---|---|---|
| WO | 2004026281 A2 | 4/2004 |
| WO | 2007137802 A2 | 12/2007 |

OTHER PUBLICATIONS

E.W.H. Jager et al., "On-chip microelectrodes for electrochemistry with moveable PPy bilayer actuators as working electrodes", Sensors and Actuators B 56 (1999) 73-78.

(Continued)

*Primary Examiner* — Kevin C Sirmons
*Assistant Examiner* — Brandy C Scott
(74) *Attorney, Agent, or Firm* — Mayer & Williams PC; David B. Bonham; Keum J. Park

(57) ABSTRACT

In accordance with one aspect, the invention relates to medical devices which comprise at least one reservoir, a therapeutic-agent-containing region disposed within the reservoir and an electrode comprising a conductive polymer. The devices of the invention are configured such that a rate of release of the therapeutic agent from the reservoir changes upon a change in the oxidation state of the conductive polymer.

25 Claims, 12 Drawing Sheets

OTHER PUBLICATIONS

D.L. Pile et al., "Electrochemically modulated transport through a conducting polymer membrane", Journal of Membrane Science 208 (2002) 119-131.
Robert S. Schwartz et al., "Preclinical Restenosis Models and Drug-Eluting Stents Still Important, Still Much to Learn", JACC vol. 44, No. 7, 2004, 1373-1385.
A. Gershlick et al., "Inhibition of Restenosis With a Paclitaxel-Eluting, Polymer-Free Coronary Stent: The European evaluation of paclitaxel Eluting Stent (ELUTES) Trial", Circulation Feb. 3, 2004, 487-493.
E Camenzind, "Treatment of In-Stent Restenosis—Back to the Future?", N. Engl. J. Med. 355, 20, Nov. 16, 2006, 2149-2151.
A.S. Lee et al., "Electroactive Polymer Actuation at the Nanoscale", Nanotechnology, 2006. IEEE-NANO 2006. Sixth IEEE Conference; Jun. 2006; vol. 2, pp. 818-821.
G.J. Mishkel et al., "Long-Term Outcomes After Management of Restenosis or Thrombosis of Drug-Eluting Stents", JACC vol. 49, No. 2, 2007, 181-184.
D.J. Axel et al, "Paclitaxel Inhibits Arterial Smooth Muscle Cell Proliferation and Migration in Vitro and in Vivo Using Local Drug Delivery", Circulation. 1997;96:636-645.
U. Speck et al., "Neointima Inhibition: Comparison of Effectiveness of Non—Stent-based Local Drug Delivery and a Drug-eluting Stent in Porcine Coronary Arteries", Radiology, 240(2), Aug. 2006, 411-418.
B. Scheller et al., "Contrast media as carriers for local drug delivery Successful inhibition of neointimal proliferation in the porcine coronary stent model", European Heart Journal (2003) 24, 1462-1467.
B. Scheller et al., "Addition of Paclitaxel to Contrast Media Prevents Restenosis After Coronary Stent Implantation", JACC vol. 42, No. 8, 2003, 1415-1420.
B. Scheller et al., "Paclitaxel Balloon Coating, a Novel Method for Prevention and Therapy of Restenosis", Circulation 2004;110;810-814.
B. Scheller et al., "Treatment of Coronary In-Stent Restenosis with a Paclitaxel-Coated Balloon Catheter", N. Engl. J. Med. 355, 20, 2006, 2113-2124.
J.H. Lee et al., "Preparation and Characterization of Solvent Induced Dihydrated, Anhydrous, and Amorphous Paclitaxel", Bull. Korean Chem. Soc. 2001, 22(8), 925-928.
L. Atanasoska et al., "XPS Studies on Conducting Polymers: Polypyrrole Films Doped with Perchlorate and Polymeric Anions", Chem. Mater. 1992, 4, 988-994.
K. Naoi et al., "Quartz Crystal Microbalance Study: Ionic Motion Across Conducting Polymers", J. Electrochem. Soc., 138(2), 1991, 440-445.
U. Johanson et al., "Comparative study of the behavior of anions in polypyrrole films", Electrochimica Acta 50 (2005) 1523-1528.
J. C. Killian et al., "Polypyrrole Composite Electrodes in an All-Polymer Battery System", J. Electrochem. Soc., 143(3) 1996, 936-942.
C. Gabrielli et al., "Charge compensation process in polypyrrole studied by ac electrogravimetry", Electrochimica Acta 46 (2001) 4095-4103.
T. Komura et al, "Electron and ion transport in polypyrrole/polystyrenesulfonate composite films", Journal of Electroanalytical Chemistry 456 (1998) 121-129.
T. Osaka et al., "Effect of Polymerization Anion on Electrochemical Properties of Polypyrrole and on Li/LiClO4/Polypyrrole Battery Performance", J. Electrochem. Soc. 135(5), 1988, 1071-1077.
K. Naoi et al., "Electrochemistry of Surfactant-Doped Polypyrrole Film(I): Formation of Columnar Structure by Electropolymerization", J, Electrochem. Soc., 142(2), 1995, 417-422.
C. Arbizzani et al., "Polypyrrole: A drug-eluting membrane for coronary stents", Electrochimica Acta 52 (2007) 3274-3279.
Q. Xie et al., "EQCM studies on polypyrrole in aqueous solutions", Journal of Electroanalytical Chemistry 420 (1997) 219-225.

K. Yamada et al., "Electrochemical and Transport Properties of Templated Gold/Polypyrrole-Composite Microtube Membranes", Journal of the Electrochemical Society, 151 (1), 2004, E14-E19.
G. Alici et al., "Establishment of a biomimetic device based on tri-layer polymer actuators—propulsion fins", Bioinsp. Biomim. 2 (2007) S18-S30.
H.Xu et al., "Polymer actuator valves toward controlled drug delivery application", Biosensors and Bioelectronics 21 (2006) 2094-2099.
J.D. Madden et al., "Encapsulated polypyrrole actuators", Synthetic Metals 105 (1999) 61-64.
X. Wang et al., "Visualizing Ion Currents in Conjugated Polymers", Advanced Materials, 16(18), pp. 1605-1605 (2004).
E. Smela et al., "Volume Change in Polypyrrole Studied by Atomic Force Microscopy", J. Phys. Chem. B, 105 (2001) 9395-9405.
E. Smela, "Microfabrication of PPy microactuators and other conjugated polymer devices", J. Micromech. Microeng 9 (1999) 1-18.
W. Takashima et al., "Investigation of bi-ionic contribution for the enhancement of bending actuation in polypyrrole film", Sensors and Actuators B, 89 (2003) 48-52.
J. Causley et al., "Electrochemically-induced fluid movement using polypyrrole", Synthetic Metals 151 (2005) 60-64.
William H. Moore et al., "Transcutaneous RF-Powered Implantable Minipump Driven by a Class-E Transmitter", IEEE Trans Biomed Eng. Aug. 2006 ; 53(8): 1705-1708.
R.M. Jisr et al., "Hydrophobic and Ultrahydrophobic Multilayer Thin Films from Perfluorinated Polyelectrolytes", Angew. Chem. Int. Ed. 2005, 44,782-785.
L. Wang et al., "Formation of ordered macroporous films from fluorinated polyimide by water droplets templating," European Polymer Journal 43 (2007) 862-869.
L. Hao et al., "Fabrication of silica core—conductive polymer polypyrrole shell composite particles and polypyrrole capsule on monodispersed silica templates", Synthetic Metals, 139(2), 2003, 391-396.
S. Gupta et al., "Spherical Molecular Containers of Polypyrrole: From Discovery to Design to Drug Delivery Applications," 10th Annual NSTI Nanotech, The Nanotechnology Conference and Trade Show, Santa Clara, May 22, 2007.
N.M.M. Pires, "Activation of Nuclear Receptor Nur77 by 6-Mercaptopurine Protects Against Neointima Formation", Circulation, 2007, 493-500.
K. Ulbrich, "Polymeric anticancer drugs with pH-controlled activation," Advanced Drug Delivery Reviews, 56 (2004) 1023-1050.
Jaber G. Qasem et al, "Kinetics of Paclitaxel 2'-N-methylpyridinium Mesylate Decomposition", AAPS PharmSciTech 2003, 4(2) Article 21.
A. A. Antipov et al., "Polyelectrolyte Multilayer Capsule Permeability Control", Colloids Surf. A 2002, 198 , 2003, 535-541.
R. Okner et al., "Electrocoating of stainless steel coronary stents for extended release of Paclitaxel", Materials Science and Engineering: C, 27(3), 2007, 510-513.
A.-C. Chang and L.L. Miller, "Electrochemically Controlled Binding and Release of Salicylate, TCNQ.- and Ferrocyanide From Films of Oligomeric 3-Methoxythiophene", J. Electroanal. Chem., 247 (1988) 173-184.
B. Zinger and L. L. Miller, "Timed Release of Chemicals from Polypyrrole Films", J. Am. Chem. Soc. 1984, 106, 1984, 6861-6863.
R.L. Blankespoor et al., "Polymerized 3-Methoxythiophene. A processable Material for the Controlled Release of Anions", J. Chem. Soc., Chem. Commun., 1985, 90-92.
S.-K. Lee et al., "Experimental Analysis on the Properties of Polypyrrole as Drug Delivery System Materials," Smart Structures and Materials 2003: Electroactive Polymer Actuators and Devices (EAPAD), Yoseph Bar-Cohen, Editor, Proceedings of SPIE vol. 5051 (2003).
H. Huang et al., "Probe beam deflection study on electrochemically controlled release of 5-uorouracil", Electrochimica Acta, 43(9), 1998, 999-1004.

\* cited by examiner

MEDICAL DEVICES EMPLOYING CONDUCTIVE POLYMERS FOR DELIVERY OF THERAPEUTIC AGENTS

RELATED APPLICATIONS

This application claims the benefit of U.S. provisional patent application 61/074,456, filed Jun. 20, 2008, which is incorporated by reference herein in its entirety.

FIELD OF THE INVENTION

The present invention relates to medical devices for the delivery of therapeutic agents into human subjects.

BACKGROUND OF THE INVENTION

The delivery of a therapeutic agent onto or within the body of a patient is common in the practice of modern medicine. In vivo delivery of therapeutic agents is often implemented using medical devices that may be temporarily or permanently placed at a target site within the body. These medical devices can be maintained, as required, at their target sites for short or prolonged periods of time, delivering therapeutic agents at the target site.

SUMMARY OF THE INVENTION

In one aspect, the present invention relates to medical devices which comprise at least one reservoir, a therapeutic-agent-containing region disposed within the reservoir, and an electrode comprising a conductive polymer. The devices of the invention are configured such that a rate of release of the therapeutic agent from the reservoir changes (e.g., release begins, increases, decreases, ceases, etc.) upon a change in the oxidation state of the conductive polymer.

An advantage of the present invention is that medical devices may be provided in which therapeutic agent delivery is electrically assisted, and therefore controllable.

These and other aspects, embodiments and advantages of the present invention will become readily apparent to those of ordinary skill in the art upon review of the Detailed Description and any claims to follow.

BRIEF DESCRIPTION OF THE DRAWINGS

FIG. 16A illustrates the device after loading with a therapeutic agent and before swelling of the conductive polymer electrodes. FIG. 16B illustrates the device of FIG. 16A after swelling of the conductive polymer electrodes such that the therapeutic agent is held in the device. FIG. 16 C illustrates the device of FIG. 16B after shrinking the conductive polymer electrodes in vivo, allowing the therapeutic agent to be released from the device.

DETAILED DESCRIPTION

Figure 1A:
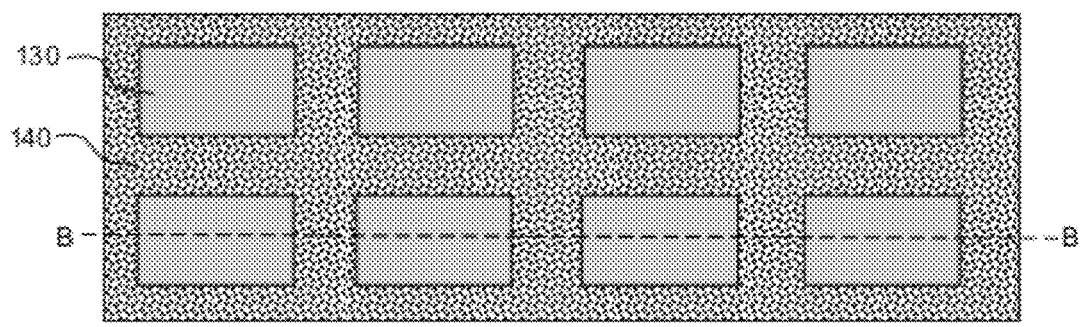
FIGS. 1A and 2A are schematic top views of a portion of a surface of a medical device in accordance with an embodiment of the invention in which the conductive polymer electrodes are biased such that the conductive polymer electrodes are in contracted and expanded states, respectively.

A more complete understanding of the present invention is available by reference to the following detailed description of various aspects and embodiments of the invention. The detailed description of the invention which follows is intended to illustrate but not limit the invention. The scope of the invention is defined by any appended claims.

In accordance with one aspect, the invention relates to medical devices which comprise at least one reservoir, a therapeutic-agent-containing region disposed within the reservoir, and an electrode comprising a conductive polymer (also referred to herein as a "conductive polymer electrode"). The devices of the invention are configured such that a rate of release of the therapeutic agent from the reservoir changes (e.g., release begins, release increases, release decreases, release ceases, etc.) upon a change in the oxidation state of the conductive polymer.

The devices of the invention are typically configured such that changes in the conductive polymer electrode as a result of a change in oxidation state (e.g., swelling, shrinkage, change in hydrophobicity/hydrophiliciy, etc.) leads to a change in the rate of release. In many instances, the conductive polymer is positioned within the reservoir (including the mouth of the reservoir in certain embodiments). For example, the conductive polymer may define at least a portion of the internal surface of the reservoir (e.g., forming or lining the interior of the reservoir, including the mouth in certain embodiments).

Medical devices benefiting from the present invention are numerous and may be selected, for example, from the following: patches for delivery of therapeutic agent to intact skin and broken skin (including wounds), implantable or insertable medical devices such as catheters (e.g., renal or vascular catheters such as balloon catheters), balloons, guide wires, filters (e.g., vena cava filters and mesh filters for distil protection devices), stents (including coronary vascular stents, peripheral vascular stents, cerebral, urethral, ureteral, biliary, tracheal, gastrointestinal and esophageal stents), stent coverings, stent grafts, vascular grafts, abdominal aortic aneurysm (AAA) devices (e.g., AAA stents, AAA grafts), vascular access ports, embolization devices including cerebral aneurysm filler coils (such as Guglilmi detachable coils and various other metal coils), myocardial plugs, septal defect closure devices, implantable patches, drug depots that are adapted for placement in an artery for treatment of the portion of the artery distal to the device, pacemakers and pacemaker leads, defibrillation leads and coils, neurostimulation leads, ventricular assist devices including left ventricular assist hearts and pumps, total artificial hearts, heart valves, vascular valves, anastomosis clips and rings, cochlear implants, tissue bulking devices, tissue engineering scaffolds for in vivo tissue regeneration, especially neural pathway regeneration, such as the spinal cord, joint prostheses, spinal discs and nuclei, orthopedic prosthesis such as bone grafts, bone plates, fins and fusion devices, orthopedic fixation devices such as interference screws in the ankle, knee, and hand areas, rods and pins for fracture fixation, screws and plates for craniomaxillofacial repair, dental implants, biopsy devices, as well as many other devices that are implanted or inserted into the body and from which therapeutic agent is released.

The medical devices of the present invention include medical devices that are used for diagnosis, for systemic treatment, or for the localized treatment of any tissue or organ, for example, the following: tumors; organs including the heart, coronary and peripheral vascular system (referred to overall as "the vasculature"), the urogenital system, including kidneys, bladder, urethra, ureters, prostate, vagina, uterus and ovaries, eyes, lungs, trachea, esophagus, intestines, stomach, brain, liver and pancreas, skeletal muscle, smooth muscle, breast, dermal tissue, and cartilage. As used herein, "treatment" refers to the prevention of a disease or condition, the reduction or elimination of signs or symptoms associated with a disease or condition, or the substantial or complete elimination of a disease or condition. Typical subjects (also referred to as "patients") are vertebrate subjects, more typically mammalian subjects, and even more typically human subjects.

As noted above, in one aspect, the invention relates to medical devices which comprise at least one reservoir, a therapeutic-agent-containing region disposed within the reservoir and an electrode comprising a conductive polymer (also referred to herein as a "conductive polymer electrode").

Note that in the devices of the present invention, the therapeutic-agent-containing region is distinct from the conductive polymer electrode. In some embodiments, however, the conductive polymer electrode may contain a therapeutic agent, whereas in other embodiments the conductive polymer electrode does not contain a therapeutic agent.

The devices of the invention are configured such that a rate of release of the therapeutic agent from the reservoir changes (e.g., release begins, release increases, release decreases, release ceases, etc.) upon a change in the oxidation state of the conductive polymer. More particularly, the devices of the invention are configured such that changes in the conductive polymer electrode as a result of the change in oxidation state (e.g., swelling, shrinkage, a change in hydrophobicity/hydrophiliciy, etc.) leads to a change in the rate of release.

The oxidation state of a conductive polymer within a conductive polymer electrode may be changed by application of a suitable potential between the conductive polymer electrode and an additional electrode (also referred to herein as a "counter-electrode"). The following elements are generally utilized in this process: (a) the conductive polymer electrode, (b) the counter-electrode, (c) an electrolyte in contact with both the conductive polymer electrode and the counter-electrode, and (d) a source of electrical potential (also referred to herein as a "power supply").

The electrolyte, which is in contact with at least a portion of the surface of the conductive polymer, allows for the flow of ions and thus acts as a source/sink for the ions. The electrolyte may be, for example, a liquid, a gel, or a solid, so long as ion movement is permitted. In various embodiments of the invention, physiological fluid is used as the electrolyte.

The counter-electrode may be disposed on or in the medical device, or it may be in the form of a distinct device. Counter-electrodes may be formed from any suitable conductive material. Examples of conductive materials for counter-electrodes include suitable members of the following, among many others: conductive polymers, pure metals and metal alloys (e.g., gold, platinum, stainless steel, etc., due to their high conductivity, oxidation resistance, and radiopacity, which may facilitate visibility of the device during fluoroscopy or the like, or magnesium or magnesium alloy, which can be left in the tissue where it will eventually oxidize in vivo), and conductive carbon. Counter electrodes may take on innumerable shapes, including layers, rods, wires, tubes, blades, and grids, among many others. Designs maximizing the area of contact between the counter-electrode and the electrolyte may improve charge transfer and reduce activation time.

In certain embodiments, the oxidation state of the conductive polymer is changed with the assistance of a reference electrode (e.g., a silver/silver chloride electrode). Like the counter-electrode, where employed, the reference electrode may be disposed on or in the medical device, or it may be in the form of a distinct device. In one embodiment, an Ag/AgCl reference electrode may be formed on a medical device using a process described in E. W. H. Jager et al., *Sensors and*

*Actuators B* 56 (1999) 73-78. Specifically, an Ag/AgCl reference electrode may be formed by depositing (e.g., by electroplating or another deposition process) an Ag layer on the device (e.g., on a gold conductor layer), followed by partial conversion of the Ag layer to AgCl electrochemically, for example, by applying a suitable potential to the electrode while immersed in a KCl electrolyte solution (using a suitable counter-electrode).

A power supply may be, for example, provided within the medical devices of the invention or may be in the form of a separate device that is connected to the medical devices of the invention (e.g., via insulated conductive lines). In some embodiments, the conductive polymer electrode, the counter-electrode and/or the reference electrode are configured for readily connection to a power supply (e.g., via insulated conductive lines that terminate in suitable electrical coupling components, such as plugs, sockets, etc.).

In certain devices of the invention, particularly implants, power may be provided in the form of a wireless system. For example, a device may be provided with a circuit that includes a conductive coil with a diode bridge in which one end is connected to one or more conductive polymer electrodes and another end is connected to one or more counter-electrodes. Such a system can be activated using an external power transmitter such as an RF transmitter. See, e.g., William H. Moore et al., *IEEE Trans Biomed Eng.* 2006 August; 53(8): 1705-1708. Suitable frequencies range, for example, from 1 Mhz to 20 MHz. In certain embodiments, one may include additional electronic components, such as a reference electrode and/or a voltage regulating device. A very useful component that can be used for this purpose is a Zener diode. Zener diodes are widely used to regulate the voltage across a circuit. When connected in parallel with a variable voltage source (e.g., a coil/diode arrangement like that previously described) so that it is reverse biased, a Zener diode begins to conduct current when the voltage reaches the diode's reverse breakdown voltage. From that point it maintains the voltage at that value. In other words, when receiving a variable voltage from a conductive coil, one can assure a fixed voltage across the electrodes regulating therapeutic agent release. Additional electronic components that may be employed include sensing devices (e.g., current and/or voltage sensing devices) and transmitters. With such components, one can communicate values (e.g., current and/or voltage values) back to the external power transmitter, allowing one to adjust the same. Such embodiments may be especially suitable for the larger implants (e.g., heart valves, tissue bulking and regeneration devices, etc.).

A conductive polymer electrode may be formed using any suitable conductive polymer. Known conductive polymers include polypyrrole and its derivatives and copolymers, polythiophene and its derivatives and copolymers, including poly (3-alkyl thiophenes) and poly(3,4-ethylenedioxythiophene) (PEDOT), polyaniline and its derivatives and copolymers, poly(p-phenylene vinylene) and its derivatives and copolymers, polysulfone and its derivatives and copolymers, and polyacetylene and its derivatives and copolymers. Polypyrrole is one of the more stable of these polymers under physiological conditions. Known derivatives of polypyrrole include the following substituted polymers: poly(N-methylpyrrole), poly(N-butylpyrrole), poly[N-(2-cyanoethyl)pyrrole], poly[N-(2-carboxyethyl)pyrrole], poly(N-phenylpyrrole), poly[N-(6-hydroxyhexyl)pyrrole], and poly[N-(6-tetrahydropyranylhexyl)pyrrole], among others.

Conductive copolymers may be formed from the above and other monomers (e.g., from pyrrole monomers, thiophene monomers, aniline monomers, p-phenylene vinylene monomers, sulfone monomers, acetylene monomers, etc). For instance, pyrrole copolymers can be formed, for example, from two or more of the following monomers: pyrrole, 1-(2-cyanoethyl)pyrrole, 1-phenylpyrrole, 3-(acetic acid)pyrrole, 1-(propionic acid)pyrrole, and the pentafluorophenol ester of the same, among others. Specific examples include, for example poly[pyrrole-co-3-(acetic acid)pyrrole], poly[pyrrole-co-1-(propionic acid)pyrrole], poly[pyrrole-co-1-(propionic acid)pyrrole pentafluorophenol ester], poly[pyrrole-co-1-(2-cyanoethyl)pyrrole] and poly(pyrrole-co-1-phenylpyrrole), among others.

Conductive polymers are typically semi-conductors in their neutral state. However, upon oxidation or reduction of the polymer to a charged state (e.g., polypyrrole is positively charged when oxidized and is neutral when reduced), the electrical conductivity is understood to be changed from a semi-conductive regime to a semi-metallic regime. Without wishing to be bound by theory, oxidation and reduction are believed to lead to charge imbalances that, in turn, can result in a flow of ions into or out of the material. These ions typically enter/exit the material from/into an ionically conductive medium adjacent to the polymer. It generally believed that dimensional changes are effectuated in conductive polymers by the mass transfer of the ions into or out of the polymers. For example, in some conductive polymers, expansion is believed to be due to ion insertion between chains, whereas in others, inter-chain repulsion is believed to be the dominant effect. Regardless of the mechanism, this ion movement results in expansion or contraction of the polymer which can deliver significant stresses and strains. For example, E. Smela et al., "Volume Change in Polypyrrole Studied by Atomic Force Microscopy," *J. Phys. Chem. B,* 105 (2001) 9395-9405, have reported an increase in film thickness by over 35% for polypyrrole in the reduced state compared to the oxidized state.

Redox switching of conductive polymers may allow a number of different oxidation states to be accessible. These redox states are stabilized by charge-balancing counter ions (often called dopant ions), which move in and out of the polymer during electrochemical switching. As a specific example, a variety of charge-balancing anions may be associated with an oxidized, positively charged, conductive polymer, such as polypyrrole, for example, during electropolymerization. However, by reducing/neutralizing the polymer, a net negative charge develops within the polymer.

If the dopant anions are substantially mobile (e.g., where the anions are small molecules), the development of the net negative charge upon reduction/neutralization of the polypyrrole results primarily in expulsion of the anions from the polymer into the adjacent ionically conductive medium, shrinking the polymer. Examples of mobile ions that are commonly used in the formation of polypyrrole include perchlorate ($ClO_4^-$), $BF_4^-$, $Br^-$, $Cl^-$, $NO_3^-$, and $I^-$. Naturally occurring ions (in the body) such as chloride ions may be preferred from a biological point of view.

If the dopant anions are substantially immobile (e.g., where the anions are large molecules), the development of the net negative charge upon reduction/neutralization of the polypyrrole results primarily in an influx of cations from the adjacent ionically conductive medium, expanding the polymer. Examples of substantially immobile anions that are commonly used in the formation of polypyrrole include dodecylbenzene sulfonate, polyvinyl sulfonate, poly-4-styrene sulfonate, polyaspartic acid, and polyglutamic acid. Examples of mobile cations include naturally occurring (in the body) cations such as $Na^+$ and $K^+$, among others.

It is noted that dodecylbenzene sulfonate is a surfactant having a hydrophilic (charged) end and hydrophobic (hydrocarbon) end. Reduction/neutralization of polypyrrole in which dodecylbenzene sulfonate is used as the dopant ion has been observed to cause an increase in hydrophilicity, which has been hypothesized to be the result of the repulsion of the charged end of the surfactant from the polymer bulk to the surface (i.e., the interface with the ionically conductive medium), such that the concentration of the hydrophilic charged end groups increases at the surface. Conversely, oxidation of the of polypyrrole has been observed to cause an increase in hydrophobicity, which has been hypothesized to be the result of withdrawal of the charged end of the surfactant into the polymer bulk, leading to an increase in concentration of the hydrophobic end of the surfactant at the surface. Regardless of the mechanism, dodecylbenzene-sulfonate-doped polypyrrole is observed to swell and become more hydrophilic upon reduction/neutralization and is observed to shrink and become more hydrophobic upon oxidation. See, e.g., J. Causley et al., "Electrochemically-induced fluid movement using polypyrrole," *Synthetic Metals* 151 (2005) 60-64.

If the dopant anions are moderately mobile (e.g., where the medium-sized anions such as tosylate anions are employed), motion of both cations and anions have been observed during redox processing. K. Naoi et al., *J. Electrochem. Soc., Vol.* 138, No. 2, February 1991, pp. 440-445.

Various conductive polymers can be formed by electropolymerization. For instance, pyrrole monomers may be electropolymerized in the presence of a suitable anionic material (e.g., one of the anionic doping materials discussed above, among others). A typical apparatus for carrying out electropolymerization includes the following: an anode (e.g., a conductive metal surface upon which electropolymerization takes place), a cathode (e.g., a metallic counter-electrode) and, frequently, a reference electrode, each separated by an electrolyte (e.g., a solution containing pyrrole and a suitable doping anion), as well as a potentiostat which monitors/sets the voltages/currents at the various electrodes. Electropolymerization can be carried out under a variety of electrochemical conditions including the following, among others: (a) constant current (galvanostatic), (b) constant voltage (potentiostatic), (c) current scan/sweep, e.g., via a single or multiple scans/sweeps, (d) voltage scan/sweep, e.g., via a single or multiple scans/sweeps, (e) current square waves or other current pulse wave forms, (f) voltage square waves or other voltage pulse wave forms, and (g) a combination of different current and voltage parameters.

For further regarding conductive polymers, see, e.g., Pub. Nos. US 2006/0184092 to Atanasoska et al. and US 2007/0239256 to Weber et al., as well as the references cited therein.

As noted above, in some embodiments of the invention, the conductive polymer electrode may contain a therapeutic agent. As a specific example, the conductive polymer electrode may contain an anionic therapeutic agent, which is incorporated into the electrode during electrodeposition of the conductive polymer. As another specific example, a small mobile anion may be incorporated into the electrode during electrodeposition of the conductive polymer. The conductive polymer is then oxidized and reduced over multiple cycles while in contact with an electrolyte that contains an anionic therapeutic agent, resulting in an anion exchange between the as-deposited anions and the anionic therapeutic agent. As another specific example, a large immobile anion may be incorporated into the electrode during electrodeposition of the conductive polymer and subsequently reduced while in contact with an electrolyte that contains a cationic therapeutic agent. Upon reduction, the cations are drawn into the conductive polymer.

Various embodiments of the invention will now be discussed. In some embodiments, the conductive polymer electrode is disposed within the reservoir such that, when the conductive polymer swells (e.g., upon conductive polymer oxidation or reduction, depending on the nature of the conductive polymer), the volume of the reservoir is reduced, urging the therapeutic agent from the reservoir. In some embodiments, the conductive polymer electrode is disposed within the reservoir such that, when the conductive polymer contracts (e.g., upon conductive polymer oxidation or reduction), the volume of the reservoir is reduced, urging the therapeutic agent from the reservoir. In some embodiments, the conductive polymer electrode is disposed within the reservoir such that, when the hydrophilicity/hydrophobicity of the conductive polymer changes (e.g., upon conductive polymer oxidation or reduction) the therapeutic agent is urged from the reservoir. In some embodiments, the conductive polymer electrode is disposed within the reservoir such that, when the conductive polymer contracts (e.g., upon conductive polymer oxidation or reduction), the mouth of the reservoir is enlarged, commencing or increasing the rate of therapeutic agent delivery from the reservoir. In some embodiments, two or more of the preceding mechanisms are employed to modify the rate of therapeutic agent delivery from the reservoir.

Several embodiments will now be discussed in which the conductive polymer electrode is disposed within the reservoir such that, when the conductive polymer swells, the volume of the reservoir is reduced, urging the therapeutic agent from the reservoir. In certain of these embodiments, the conductive polymer at least partially defines the boundary (walls) of the reservoir (e.g., the reservoir is formed in the conductive polymer, a layer of the conductive polymer lines the reservoir, etc.).

In various embodiments, the medical devices of the invention comprise an underlying substrate material which may be, for example, a polymeric substrate material, a metallic substrate material, or a non-metallic substrate material such as a ceramic material, carbon-based material, or silicon-based material, among many other possibilities.

As a specific example, in certain particular embodiments, the medical devices of the invention are balloon catheters having therapeutic-agent-loaded balloon surfaces. The substrate materials for such therapeutic-agent-loaded balloon surfaces include non-compliant substrate materials (e.g., metallic materials or non-compliant polymeric materials such as polyether-polyamide block copolymers, for instance a poly (tetramethylene oxide)-polyamide-12 block copolymer, available from Elf Atochem as PEBAX) and compliant substrate materials (e.g., a compliant polymeric material such as silicon rubber, polyurethane, latex or polyisoprene. In this regard, the invention may be employed in conjunction with a wide variety of balloon catheters, including those with compliant balloons, non-compliant balloons, fiber balloons, braided balloons and/or cutting balloons. (Note that the blades s on the cutting balloons may be used as counter-electrodes in certain embodiments of the invention.)

As will be seen from the discussion below, in many embodiments of the invention, materials are provided on or within the medical devices of the invention in the form of layers. As used herein a "layer" of a given material is a region of that material whose thickness is small (e.g., 25% or less) compared to both its length and width. As used herein a layer need not be planar, for example, taking on the contours of an underlying substrate. Layers can be discontinuous (e.g., patterned). Layers can be stacked. Terms such as "film," "layer" and "coating" may be used interchangeably herein.

Figure 1B:
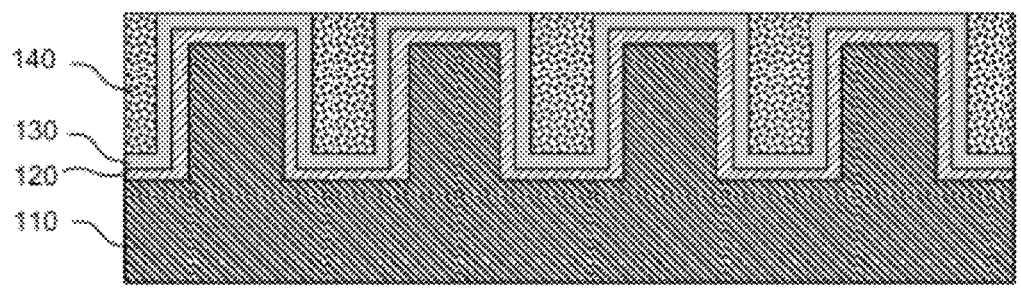
FIGS. 1B and 2B are schematic cross-sectional view taken along line B-B of FIGS. 1A and 2A, respectively.

Turning now to the drawings, FIG. 1A is a schematic top view of a portion of a medical device surface (e.g., a portion of a balloon surface, etc.) in accordance with the invention. FIG. 1B is a schematic cross-sectional view taken along line B-B of FIG. 1A. The device shown contains a substrate 110 (e.g., a compliant or non-compliant substrate material, etc.), within which are formed various depressions (e.g., trenches in the embodiment shown). Disposed over the substrate 110 is a thin metallic layer 120 (e.g., an electro-deposited, electroless-deposited, or PVD deposited gold layer, platinum layer, etc.) upon which is provided a conductive polymer electrode 130 (e.g., an electrodeposited polypyrrole layer doped with a suitable anion). The thin metallic layer 120 acts as an electrical contact for the conductive polymer electrode 130. The trenches of the resulting structure (generically referred to herein as reservoirs) are filled with a therapeutic-agent-containing material 140. A very suitable way of loading a therapeutic-agent-containing material into the reservoirs is by means of an inkjet printer or a pico-liter dispenser. Such devices have as well the advantage that one can define the amount of therapeutic-agent-containing material that is deposited into each individual reservoir.

Figure 2A:
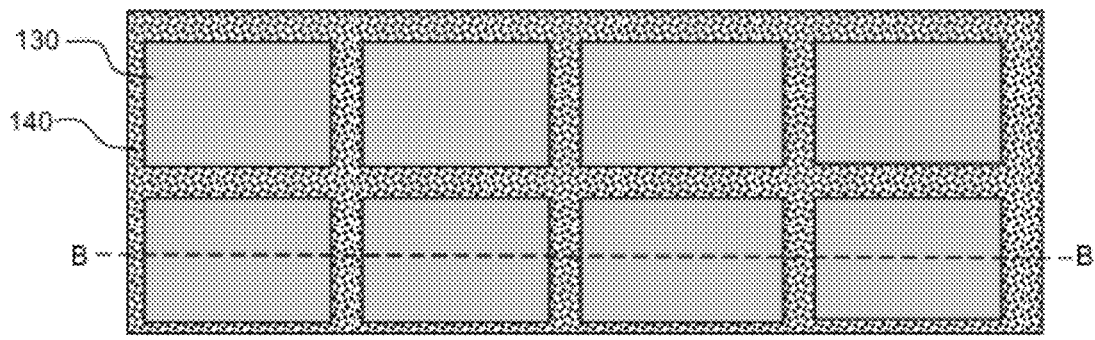
Figure 2B:
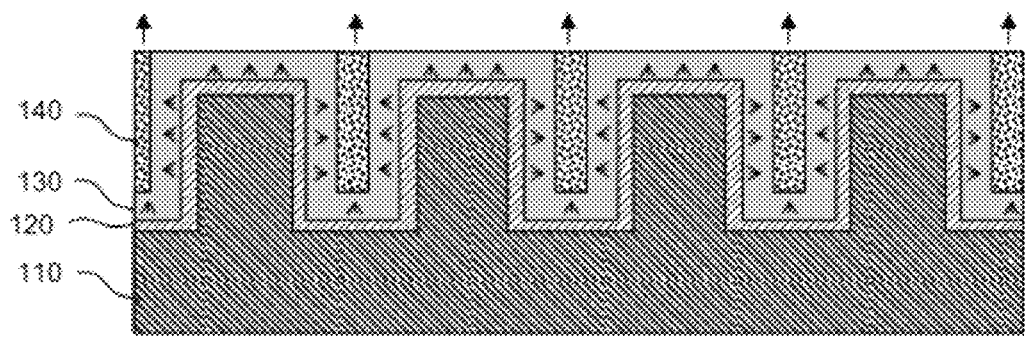

Upon application of a suitable potential between the conductive polymer electrode 130 and a counter-electrode (not shown) in the presence of a suitable electrolyte that is disposed between the conductive polymer electrode 130 and the counter-electrode (e.g., a physiological fluid such as blood, not shown), the conductive polymer within the conductive polymer electrode 130 changes its oxidation state, resulting in a swelling of the conductive polymer electrode 130 as shown in FIGS. 2A and 2B. This swelling (shown by arrows in FIG. 2B) leads to expulsion of a portion of the therapeutic-agent-containing material 140 within the reservoirs.

For example, the conductive polymer electrode 130 may comprises polypyrrole that is electrodeposited with small anions for a doping material, followed by reduction and expulsion of the ions prior to loading with the therapeutic-agent-containing material 140. Once the device is inserted into the body of a subject, the polypyrrole is oxidized, resulting in the influx of anions (e.g., $Cl^-$, etc.) from the surrounding physiological fluid and swelling of the conductive polymer electrode 130.

As another example, the conductive polymer electrode 130 may comprises polypyrrole that is electrodeposited with large substantially immobile anions for a doping material, which is not reduced prior to loading with the therapeutic-agent-containing material 140. Once the device is inserted into the body of a subject, the polypyrrole is reduced by application of a suitable potential, resulting in the influx of cations (e.g., $Na^+$, $K^+$, etc.) from the surrounding physiological fluid.

As noted above, polypyrrole that is doped with an anionic surfactant such as dodecylbenzene sulfonate is known to become more hydrophilic in the reduced state. Where the therapeutic-agent-containing material is hydrophobic (e.g., paclitaxel or another hydrophobic drug in a hydrophobic solvent medium, etc.), the increase in the hydrophilicity of the conductive polymer electrode 130 may assist in the expulsion of the therapeutic-agent-containing material based on hydrophilic-hydrophobic repulsion.

In the embodiment of the invention shown in FIGS. 1A-B and 2A-B, the substrate material is non-conductive, necessitating the application of a conductive layer prior to electropolymerization. If the substrate is conductive, on the other hand, the conductive polymer can be electropolymerized directly on the substrate.

Figure 3:
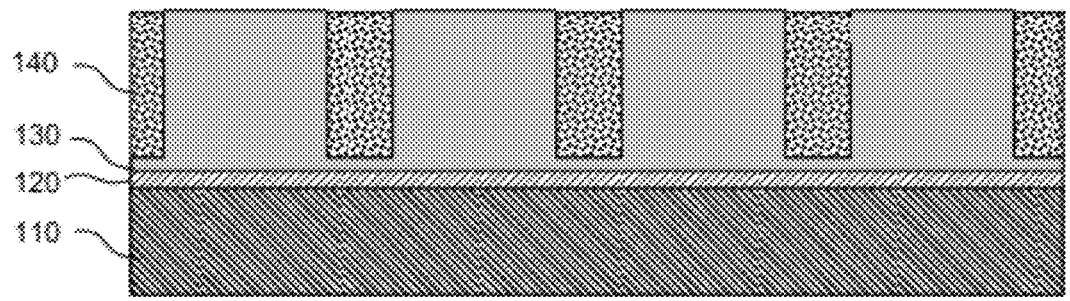
FIG. 3 is a schematic cross-sectional view taken along line B-B of FIG. 1A, in accordance with an alternative embodiment of the invention.

Numerous other variations on the above are also possible. For example, FIG. 3 is an alternative cross-section taken along line B-B of FIG. 1A. Like the cross-section of FIG. 1B, the cross-section of FIG. 3 comprises a substrate 110, a thin metallic layer 120, a conductive polymer electrode 130, and a therapeutic-agent-containing material 140. Unlike the cross-section of FIG. 1B, in which the depressions (e.g., trenches, etc.) are formed in the substrate material, however, the depressions in the cross-section of FIG. 3 are formed in the conductive polymer electrode 130.

Figure 4:
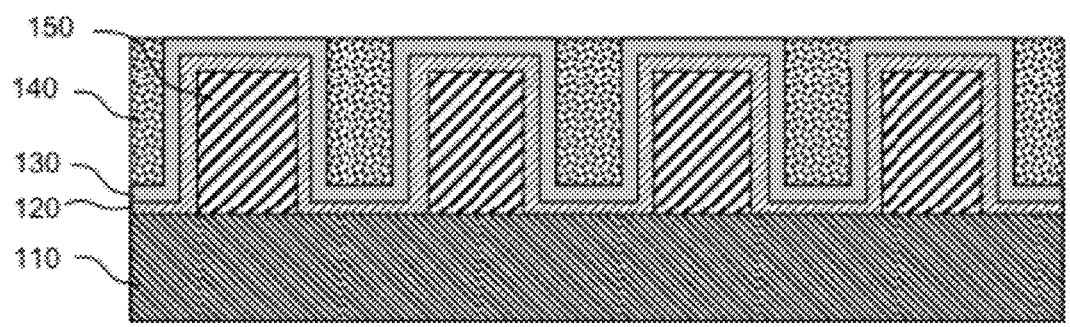
FIG. 4 is a schematic cross-sectional view taken along line B-B of FIG. 1A, in accordance with another alternative embodiment of the invention.

FIG. 4 is another alternative cross-section taken along line B-B of FIG. 1A. Like the cross-section of FIG. 1B, the cross-section of FIG. 4 comprises a substrate 110, a thin metallic layer 120, a conductive polymer electrode 130, and a therapeutic-agent-containing material 140. Unlike the cross-section of FIG. 1B, however, an additional layer of reservoir-forming material 150 is deposited on the substrate 110 in order to create the depressions (e.g., trenches, etc.). The additional layer of material 150 may be the same as the material forming the substrate 110 or it may be formed from a different material. The different material may be, for example, a polymer with a hardness that is higher than that of the electroactive polymer.

Figure 12:
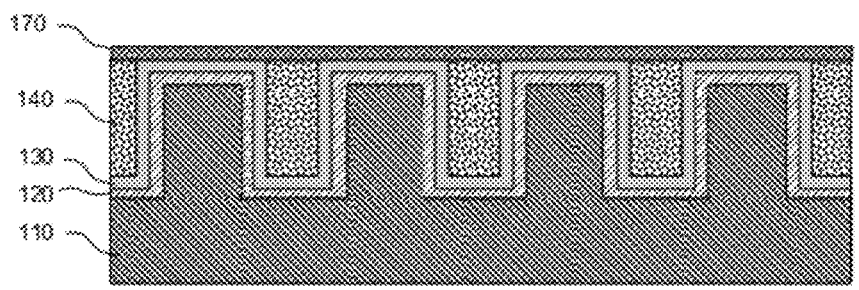
FIG. 12 is a schematic cross-sectional view of a portion of a device in accordance with another embodiment of the invention.

In certain embodiments of the invention, the therapeutic-agent-containing material within the reservoir is covered with a barrier layer to prevent premature release of the therapeutic-agent-containing material. Such embodiments may be useful, for example, where the therapeutic-agent-containing material is highly soluble and/or where it is desired for there to be a substantial period of time between placement of the medical device on or in the body, and release of the therapeutic agent. For instance, FIG. 12 illustrates a device like that of FIGS. 1A-B in that it comprises a substrate 110, a thin metallic layer 120, a conductive polymer electrode 130, and a therapeutic-agent-containing material 140. Unlike the device of FIGS. 1A-B, however, the device of FIG. 12 further comprises a barrier layer 170 which covers the mouths of the therapeutic-agent-containing depressions.

Examples of barrier materials include (a) those which are permeable to the electrolyte ions that are used to expand/swell the conductive polymer electrodes but not to the therapeutic agent and (b) those which are permeable both to the electrolyte ions that are used to expand/swell the conductive polymer electrodes and to the therapeutic agent. Specific examples of such materials include polyelectrolytes (which are preferably employed in conjunction with uncharged therapeutic agents in order to avoid electrostatic interaction between the polyelectrolyte and agent). For instance a single polyelectrolyte layer (e.g., polyacrylic acid (PAA), polyallylamine hydrochloride(PAH), heparin, etc.) or multiple layers of alternating charge (e.g., PAH\PAA, chitosan\heparin, etc.) may be applied to the surface. For hydrophobic agents, fluorinated polyelectrolytes may be employed such as $Na^+$ ion, and a

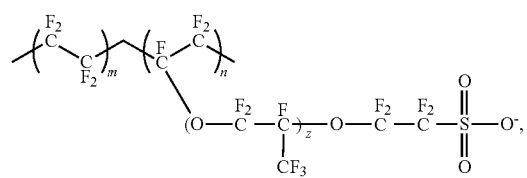

polycation synthesized from poly(vinyl pyridine) and a fluorinated alkyl iodide,

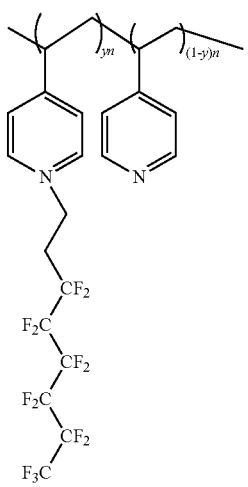

R. M. Jisr et al., *Angew. Chem. Int. Ed.* 2005, 44, 782-785.

In another specific example, a macroporous membrane may be applied to the device. In this regard, various types of polymers can be fabricated as a honeycomb-patterned film with controlled pore size, ranging from hundreds of nanometers to hundreds of microns. L. Wang et al., "Formation of ordered macroporous films from fluorinated polyimide by water droplets templating," *European Polymer Journal* 43 (2007) 862-869. Both the electrolyte ions and the therapeutic agent can diffuse through such pores, however, the bulk of the therapeutic agent is expected to remain within the reservoir until the time of expansion/swelling of the conductive polymer electrodes (assuming that the time period between introduction of the device and electrode activation is relatively short).

Further examples of barrier members include material layers that dissolve over the time frame that is employed to implant/insert the device at the position desired for drug delivery. Examples of such materials include mannitol and polyethylene glycol, among others.

In still further examples, pH sensitive material materials may be employed as barrier members to prevent premature release of therapeutic agent from the reservoirs of the device. For example, a material that is insoluble at physiological pH but soluble at slightly acidic pH or at slightly basic pH may be employed for this purpose. A nearby electrode, for example, an electrode within the reservoir or a electrode adjacent the barrier on the surface of the device, may be provided with a suitable bias to change the pH of the local environment, dissolving the material. For instance, a suitable anodic bias may be applied to supply electrogenerated acid or a suitable cathodic bias may be applied to supply electrogenerated base. In some instances, such materials may be crosslinked to provide pH swellable and contractable gels. Examples of such materials include materials which are insoluble at physiological pH and become soluble at slightly acidic pH, for instance, materials that have functional groups (e.g., amines, etc.) that become protonated and converted into charged groups (e.g., ammonium, etc.) at slightly acidic pH, causing the material to be soluble in water/blood. One specific example of a material that becomes soluble at slightly acidic pH is chitosan. Examples of such materials further include materials which are insoluble at physiological pH and become soluble at slightly basic pH, for instance, materials that have functional groups (e.g., —COOH, etc.) that become deprotonated and converted into charged groups (e.g., —COO⁻, etc.) at slightly basic pH, causing the material to be soluble in water/blood. One specific example of a material that becomes soluble at slightly basic pH is starch.

A counter-electrode is not shown in the preceding drawings. As previously indicated, a counter-electrode may be supplied in the form of a distinct device in some embodiments. In other embodiments, one or more counter-electrodes may be disposed on or in the medical device.

Figure 5:
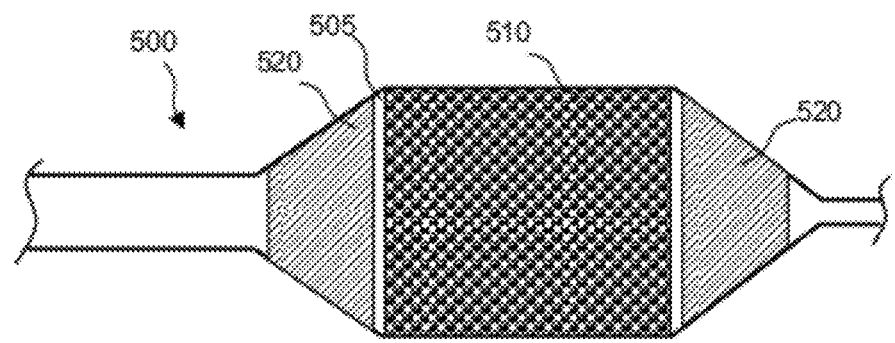
FIG. 5 is a schematic illustration of the balloon portion of a balloon catheter in accordance with an embodiment of the invention.

For example, FIG. 5 is a schematic illustration of the balloon portion of a balloon catheter 500 in accordance with the invention. The balloon catheter 500 includes a balloon 505. On the cylindrical portion of the balloon 505 is disposed a therapeutic-agent-delivering region 510 like those described elsewhere herein (which comprises at least one reservoir, a therapeutic-agent-containing region disposed within the reservoir, and a conductive polymer electrode). On the cone portions of the balloon 505 are disposed counter-electrodes 520 (e.g., gold, etc.).

Figure 6A:
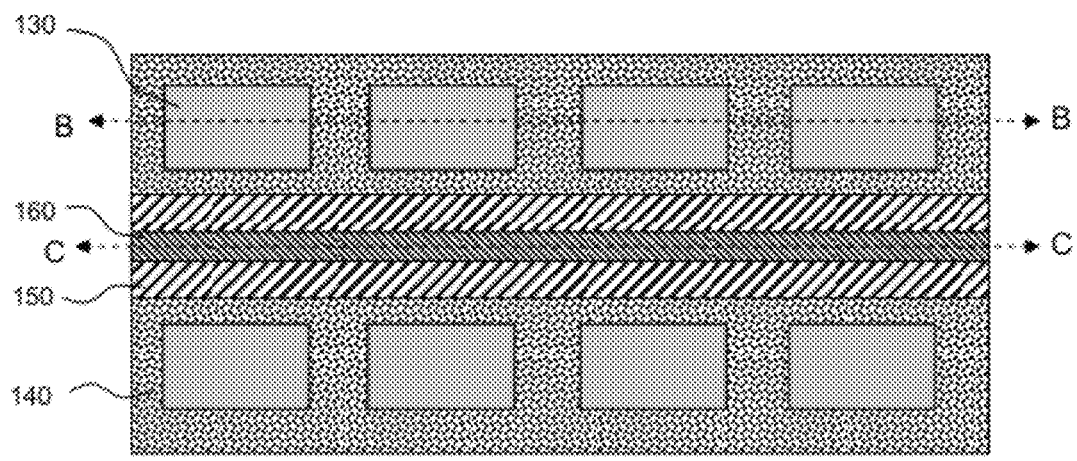
FIG. 6A is a schematic top view of a portion of a surface of a medical device in accordance with an embodiment of the invention.
Figure 6B:
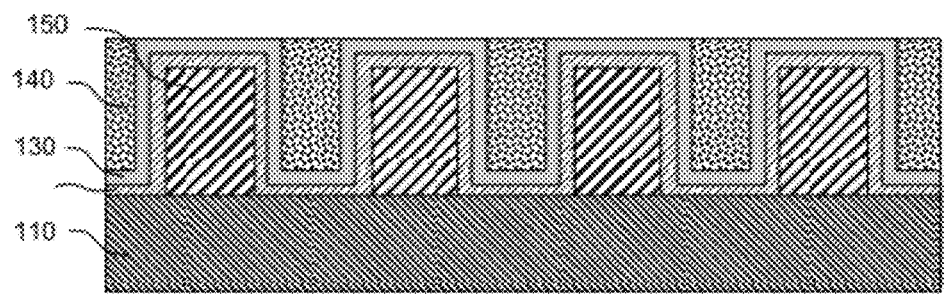
FIG. 6B is a cross-section taken along line B-B of FIG. 6A.
Figure 6C:
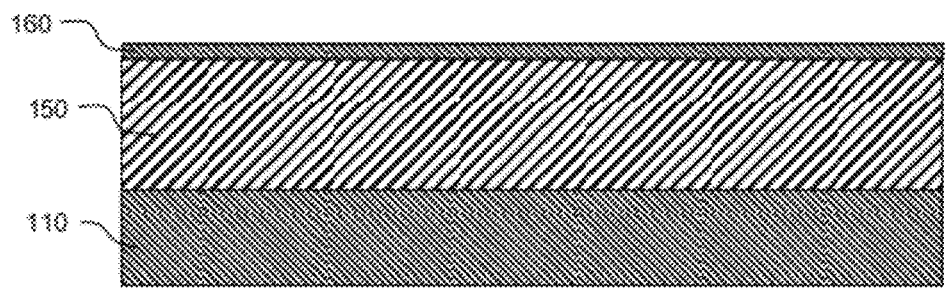
FIG. 6C is a cross-section taken along line C-C of FIG. 6A.

In other embodiments, one or more counter-electrodes are integrated into the therapeutic-agent-delivering region. For example, FIG. 6A is a schematic top view of a portion of a medical device surface (e.g., a portion of a balloon surface) in accordance with the invention. FIG. 6B is a schematic cross-sectional view taken along line B-B of FIG. 6A. As with FIG. 4 above, FIG. 6B illustrates a substrate 110, a thin metallic layer 120, a conductive polymer electrode 130, a therapeutic-agent-containing material 140, and a layer of reservoir-forming material 150 which creates the depressions. FIG. 6C is a schematic cross-sectional view taken along line C-C of FIG. 6A and illustrates a counter-electrode 160 disposed on the layer of reservoir-forming material 150, which is in turn disposed on the substrate 110. (In FIG. 6C, one could also do without layer 150 (so long as the substrate 110 is non-conductive). In addition to (or instead of) the counter-electrode 160, the device of FIGS. 6A-C may be provided with a reference electrode (e.g., an Ag/AgCl chloride electrode like that discussed above).

Where the counter-electrode is positioned on a distinct device, one may be able to preferentially change the oxidation state of the conductive polymer on specific regions of the medical device containing the reservoirs, preferentially releasing the therapeutic agent from certain regions of the medical device but not others. For example, one may wish to advance an angioplasty balloon system, with reservoirs/depots fully covering the cylindrical portion of the balloon surface, along a first guidewire into the main branch of a bifurcation in the vasculature. A distinct counter-electrode device may be positioned on a separate guidewire which is positioned in a side branch of the bifurcation. When the counter-electrode and conductive polymer electrodes on the balloon are provided with a suitable bias, the reservoirs in the vicinity of the side branch are activated faster than those opposing the side branch (due to current distribution effects).

As another example, an implant may be implanted, followed by therapeutic agent release from only a specific region on the surface of the device. For instance, one may wish to preferentially release therapeutic agent from a region of the medical device where tissue regeneration is going more slowly compared to other regions of the device. For example, one may place a counter-electrode (e.g., an insulated conductive needle with a non-insulated tip, etc.) in the vicinity of the slower regenerating area, releasing there a certain amount of therapeutic agent. The remaining drug load in the device may be equalized among the reservoirs by providing internal connections between the reservoirs.

Examples of tissue regenerating materials include, for example, growth factor stimulating hormones and factors such as progesteron, östrogen, methyl-prednisolon, triamzinolon-acetat, Corticosteroide, insulin, PDGF (platelet-derived growth factor), purpurin and activin, among others. Further examples of growth factors include, acid fibroblast growth factor (aFGF), basic fibroblast growth factor bFGF, bone morphogenetic protein (BMP), recombinant human bone morphogenetic protein (rhBMP), epidermal growth factor (EGF), hepatocyte growth factor (HGF), insulin-like growth factor I (IGF-I), nerve growth factor (NGF), transforming growth factor (TGF) and vascular endothelial growth factor (VEGF).

As seen from the above, various embodiments of the present invention involve the formation of depressions at the medical device surface, which depressions ultimately form reservoirs for the therapeutic agent. Although trenches are illustrated above, depressions may be created in a great variety of shapes and sizes. Further examples of depressions also include pores in a porous substrate. Examples include pores whose lateral dimensions are circular, polygonal (e.g., triangular, quadrilateral, penta-lateral, etc.), as well as pores of various other regular and irregular shapes and sizes. Multiple depressions can be provided in a near infinite variety of arrays. Trenches include simple linear trenches, wavy trenches, trenches formed from linear segments whose direction undergoes an angular change (e.g., zigzag trenches), and linear trench networks intersecting various angles, as well as other regular and irregular trench configurations. The depressions can be of any suitable size that provides the features of the invention. For example, the medical devices of the invention typically contain depressions whose smallest lateral dimension (e.g., the width) is less than 10 mm (10000 μm), for example, ranging from 10000 μm to 1000 μm to 100 μm to 10 μm to 1 μm to 100 nm or less.

In certain embodiments the smallest lateral dimension (e.g., the width) is on the order of 1 μm to 10 μm. For example, in addition to reporting an increase in film thickness by over 35% for polypyrrole in the reduced state compared to the oxidized state, E. Smela et al., supra, further observed that height change depended on film thickness, with films near 1.5 μm undergoing the greatest strain.

Examples of techniques for forming depressions (e.g., pores, trenches, etc.) include methods in which a material contains depressions as-formed. These include molding techniques in which a mold may be provided with various protrusions, which after casting the substrate of interest, create depressions in the material. These techniques further include techniques, such as foam-based techniques, whereby a porous material is formed. Porous materials may also be formed by removing one component from a multi-component material using a suitable process (e.g., dissolution, etching, etc.). As one specific example, porous polypyrrole layers may be formed by incorporating silica particles during polypyrrole electropolymerization (e.g., incorporating negatively charged silica particles via electrophoresis). The silica particles may then be removed from the polypyrrole, for example, along the lines described in L. Hao et al., *Synthetic Metals*, 139(2), 2003, 391-396.

As a further example of a method for forming polypyrrole, polypyrrole may be electropolymerized from a solution that contains pyrrole and a substance that functions as an electrolyte and as a surfactant as well (e.g., 2-naphthalenesulfonic acid, sodium salt). Surfactant-mediated growth using such reagents under controlled electrochemical biasing has been reported to lead to synthesis of micro/nanostructures ascribed to electrochemical polymerization of pyrrole around micelles, including cup/bowl-like containers. S. Gupta et al., "Spherical Molecular Containers of Polypyrrole: From Discovery to Design to Drug Delivery Applications," 10th Annual NSTI Nanotech, The Nanotechnology Conference and Trade Show, Santa Clara, May 22, 2007.

Examples of techniques for forming depressions further include direct removal techniques as well as mask-based removal techniques, in which masking is used to protect material that is not to be removed. Direct removal techniques include those in which material is removed through contact with solid tools (e.g., microdrilling, micromachining, etc.) and those that remove material without the need for solid tools (e.g., those based on directed energetic beams such as laser, electron, and ion beams). Mask-based techniques include those in which the masking material contacts the material to be machined (e.g., where masks are formed using known lithographic techniques) and techniques in which the masking material does not contact the material to be machined, but which is provided between a directed source of excavating energy and the material to be machined (e.g., opaque masks having apertures formed therein, as well as semi-transparent masks such as gray-scale masks which provide variable beam intensity and thus variable machining rates). Material is removed in regions not protected by the above masks using any of a range of processes including physical processes (e.g., thermal sublimation and/or vaporization of the material that is removed), chemical processes (e.g., chemical breakdown and/or reaction of the material that is removed), or a combination of both. Specific examples of removal processes include wet and dry (plasma) etching techniques, and ablation techniques based on directed energetic beams such as electron, ion and laser beams.

In still other embodiments, depressions may be formed by selective growth of a material on a substrate surface, for example, on a patterned surface or on a masked surface.

Figure 7A:
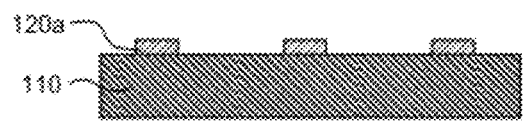
FIGS. 7A, 8, 9, 10 and 11A, are schematic cross-sectional views illustrating a method of forming a medical device, in accordance with an embodiment of the invention. The cross-section of FIG. 7A is taken along line A-A of the schematic top view of FIG. 7B. The cross-section of FIG. 11B is taken along line A-A of the schematic top view of FIG. 11A.
Figure 8:
Figure 9:
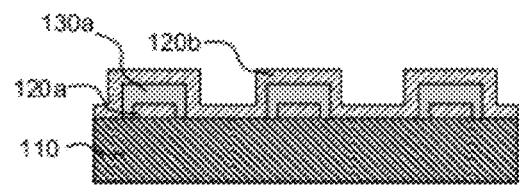
Figure 7B:
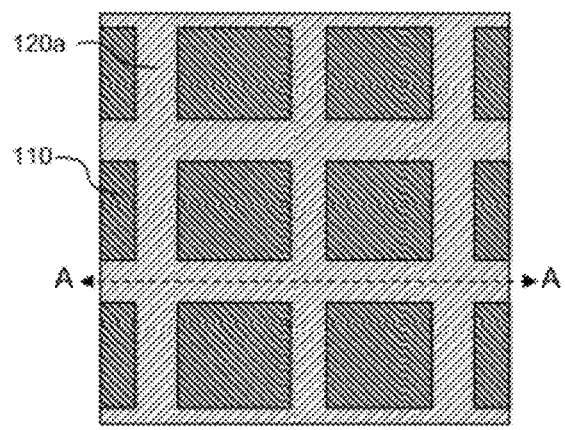
Figure 10:
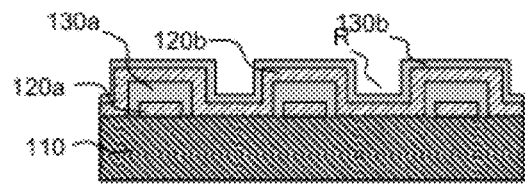
Figure 11A:
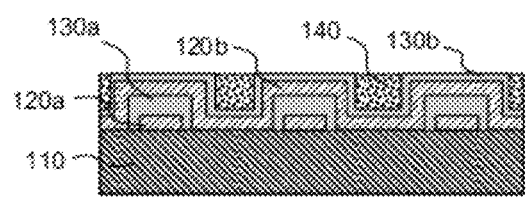
Figure 11B:
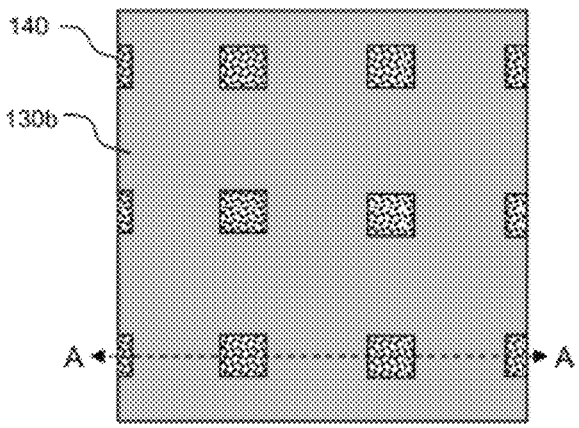

For example, FIG. 7B is a schematic top view of a portion of a substrate 110, upon which a grid of conductive material 120a (e.g., a metal) has been deposited. FIG. 7A is a cross-section of FIG. 7B, taken along line A-A. The conductive material 120 of FIGS. 7A and 7B can then be used to create an electrodeposited layer, for example, a layer of conductive polymer material 130a (e.g., doped polypyrrole) as shown in FIG. 8. This structure may be loaded with a therapeutic-agent-containing material in some embodiments (not shown). In other embodiments, the structure of FIG. 8 is then coated with a conductive layer 120b as shown in FIG. 9, upon which a layer of conductive polymer material 130b (e.g., doped polypyrrole) is formed as shown in FIG. 10. Finally the reservoirs R of FIG. 10 are filled with a therapeutic-agent-containing material 140 as shown in FIG. 11A. FIG. 11B is the top view of the device of FIG. 11A. Swelling of the upper layer of polypyrrole 130b upon oxidation or reduction of the same (depending on the anion), results in the expulsion of the therapeutic-agent-containing material 140 from the reservoirs. The lower layer of polypyrrole 130a does not swell in the embodiment shown (it is not in contact with an electrolyte), but rather is structural in nature.

In various embodiments above, therapeutic agent is delivered from the devices of the invention as a result of swelling of the conductive polymer electrode upon a change in oxidation state. In other embodiments, therapeutic agent is delivered in response to shrinking of the conductive polymer electrode upon a change in oxidation state.

For example, in many embodiments of the invention, medical devices are provided which contain reservoirs that open at reservoir mouth to the exterior of the device. The mouth of the reservoirs in these embodiments may be provided with a conductive polymer electrode that restricts the flow of therapeutic agent when swelled and allows the flow of therapeutic agent when shrunk. In other words the mouth of the reservoir is widened upon conductive polymer shrinkage and narrowed (closed in some instances) upon conductive polymer expansion.

Figure 13A:
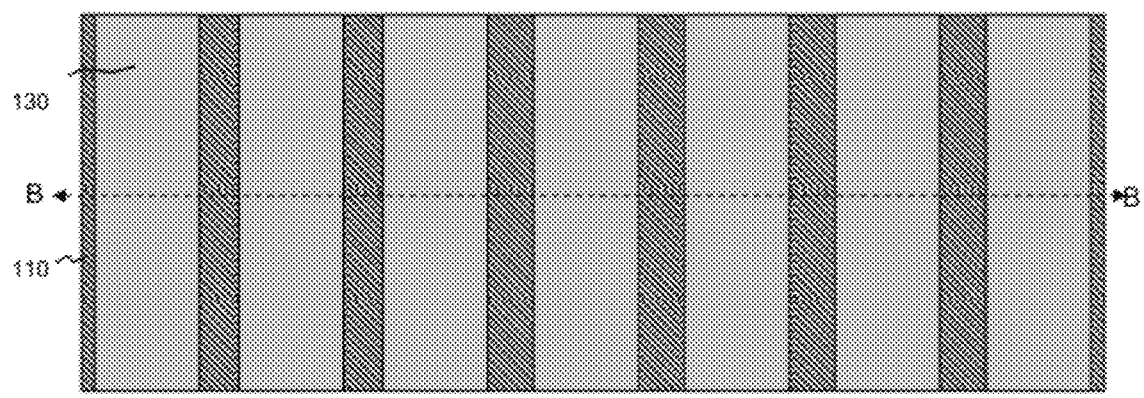
FIG. 13A is a schematic top view of a portion of a surface of a medical device in accordance with an embodiment of the invention.
Figure 13B:
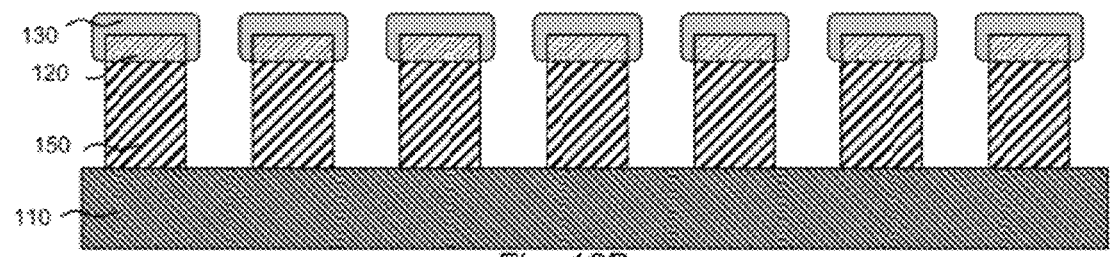
FIG. 13B is a schematic cross-section taken along line B-B of FIG. 13A.
Figure 13C:
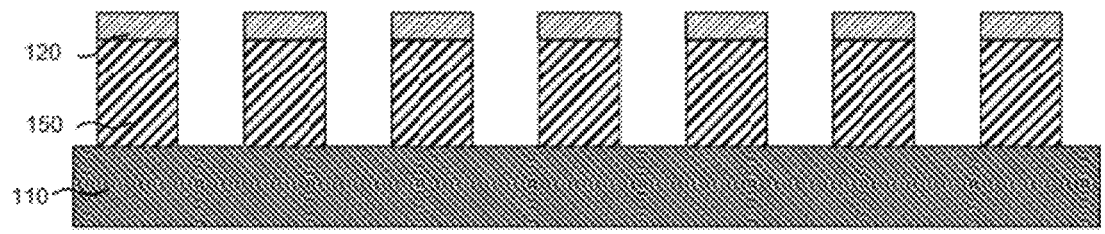
FIG. 13C corresponds to the schematic cross-section of FIG. 13B, prior to the formation of conductive polymer electrodes.
Figure 14A:
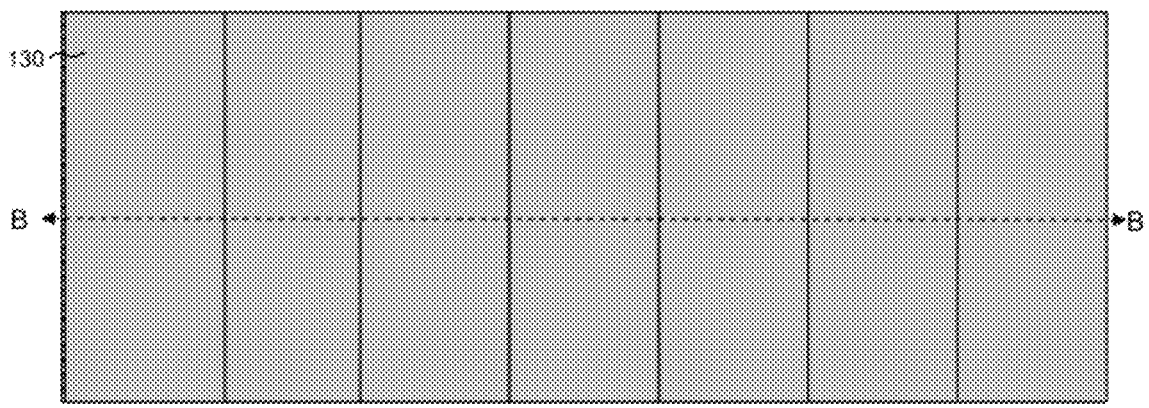
FIG. 14A is a schematic top view corresponding to the device of FIG. 13A, after loading the device with a therapeutic agent and actuation of the conductive polymer electrodes.
Figure 14B:
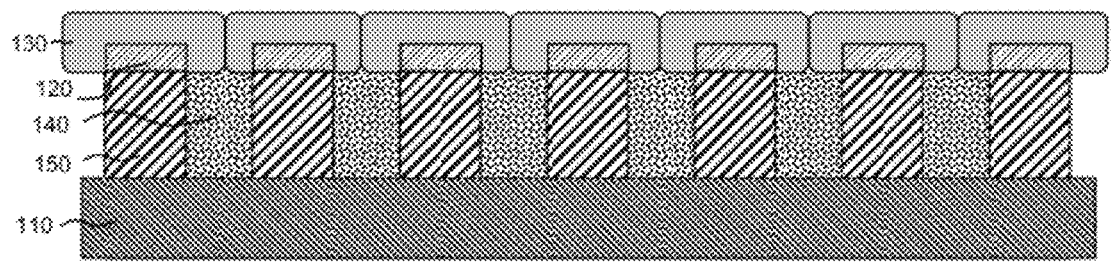
FIG. 14B is a schematic cross-section taken along line B-B of FIG. 14A.

One example of such a device is illustrated in FIGS. 13A-B. FIG. 13A is a schematic top view of a portion of a medical device surface in accordance with the invention (e.g., a portion of a balloon surface, etc.), prior to loading the reservoirs with a therapeutic-agent-containing material. FIG. 13B is a schematic cross-sectional view taken along line B-B of FIG. 13A. FIG. 13B illustrates a substrate 110, a layer of depression-forming material 150 (forming reservoirs R), a conductive layer 120 (e.g., a metallic layer) on top of depression-forming layer 150, and a conductive polymer electrode 130 formed on the conductive layer 120. The structure may be formed, for example, by depositing layers of depression-forming material 150 (e.g., a polymer) and conductive material 120 (e.g., a metal) over the entire substrate 110, followed by masking, etching the depression-forming material 150 and the conductive material 120, and mask removal, to form a structure like that of FIG. 13C. Then, an electropolymerization process is conducted to produce conductive polymer electrodes 130. The conductive polymer electrodes 130 of FIGS. 13A-B are in a contracted state, allowing the structure to be loaded with a therapeutic-agent-containing material 140, followed by expansion of the electrodes 130 to entrap the therapeutic-agent-containing material 140 as shown in FIGS. 14A-B. (FIG. 14B is schematic top view of the therapeutic-agent-loaded structure, and FIG. 14A is a schematic cross-sectional view taken along line A-A of FIG. 14B.) Upon implantation of the device in vivo, the conductive polymer electrodes 130 can be re-shrunk to a configuration analogous to that of FIG. 13A-B, allowing the release of the therapeutic agent.

K. Yamada et al., *Journal of The Electrochemical Society*, 151 (1), 2004, E14-E19 describe a process whereby submicron pore walls (and outer surfaces) of a polyester filter membrane were first plated with gold using an electroless plating process, followed by the electropolymerization of polypyrrole on the pore walls (and outer surfaces). They found that the thickness of the electrodeposited polypyrrole within the pores is not constant with pore depth. Rather they found that the polypyrrole walls were thicker at the membrane surface than in the center of the membrane, and they postulated that such "bottlenecking" occurs because the rate of polypyrrole synthesis is faster at the membrane surface than deep within the pores, a situation which they found to occur when the rate of deposition of the polypyrrole exceeds the rate of mass transport of the precursor material (pyrrole monomer) down the pore.

Figure 15:
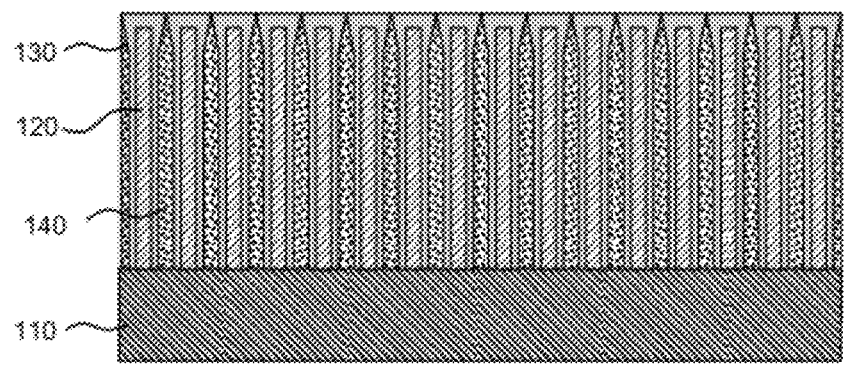
FIG. 15 is a schematic cross-section view of a portion of a medical device in accordance with another embodiment of the invention.

Similar conditions may be employed to provide therapeutic-agent-delivering devices in accordance with the present invention. For example, FIG. 15 is a schematic cross-section of a portion of a medical device which includes a (non-conductive) substrate material 110 and a layer of porous conductive material 120 disposed on the substrate. A conductive polymer electrode 130 (e.g., polypyrrole along with a substantially immobile polymeric anion) has been polymerized on the conductive material 120 under conditions such that the thickness of the deposited layer 130 is greater at the surface of the device than within the pores. (As elsewhere herein, to the extent that the porous material is non-conductive, it may be rendered conductive by depositing a layer of conductive material on the porous material—see, e.g., the electroless plating process described in K. Yamada et al. above.) After loading the device with a therapeutic-agent-containing material 140, the conductive polymer 130 is swelled (e.g., by reducing the polypyrrole while it is in contact with a cationic electrolyte) to produce the device illustrated in FIG. 15. Upon delivery to a patient, the rate of therapeutic agent release from the device can be commenced/increased by oxidizing the conductive polymer 130, which reopens the pores at the surface of the device.

Figure 16A:
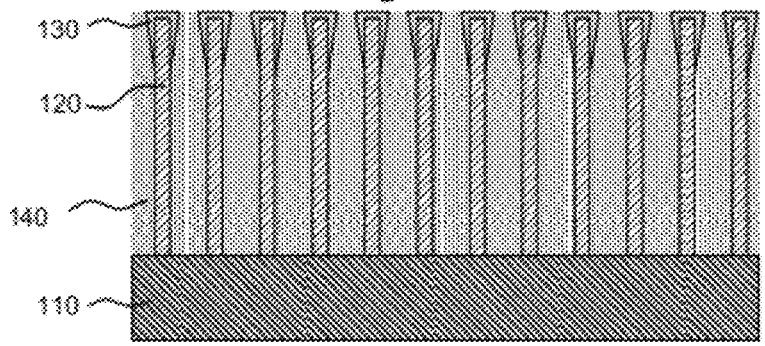
FIGS. 16A-C are schematic cross-sectional views of a portion of a medical device in accordance with yet another embodiment of the invention.
Figure 16B:
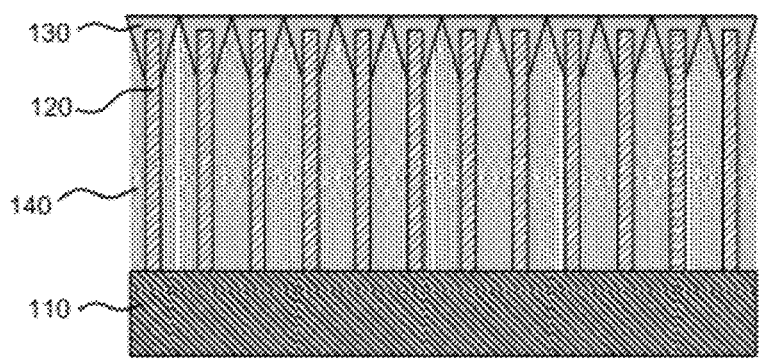
Figure 16C:
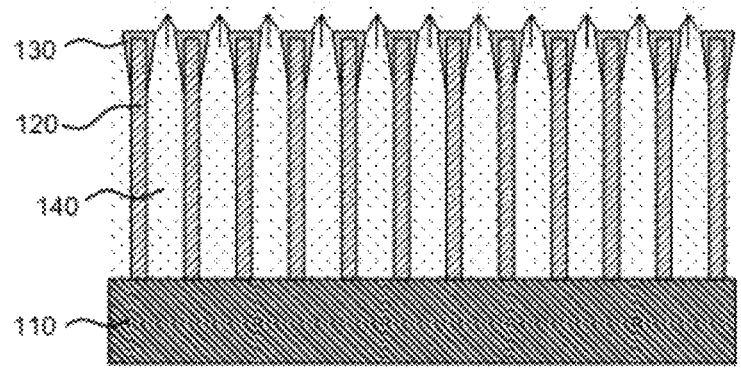

In embodiments analogous to that of FIG. 15, there is no need for the conductive polymer to cover the entire sidewall of the pores. Rather, it is only desired to provide the conductive polymer at the mouth of the pores. For example, FIG. 16A is a schematic cross-section of a portion of a medical device which, like FIG. 15, includes a substrate material 110 and a porous layer of conductive material 120 disposed on the substrate. Unlike FIG. 15, a conductive polymer 130 (e.g., polypyrrole along with a substantially immobile polymeric anion) is deposited on the device surface and at the mouth of the pores, but not deep within the pores. The pores are loaded with a therapeutic agent 140 as shown in FIG. 6A. After loading this loading process, the structure of FIG. 6A is subjected to conditions that lead to swelling of the conductive polymer 130 (e.g., by reducing the polypyrrole while it is in contact with cations in an electrolyte), closing (or narrowing) the mouths of the pores as shown in FIG. 16B. Upon delivery to a patient, the rate of therapeutic agent release from the device can be commenced/increased by oxidizing the conductive polymer 130, which opens the pores at the surface of the device, allowing the therapeutic agent 140 to exit the device. See, e.g., FIG. 16C.

Another example of a device whereby therapeutic agent is delivered in response to shrinking of a conductive polymer electrode will now be described in conjunction with the schematic cross-sectional illustrations of FIGS. 17A-17I.

Figure 17A:
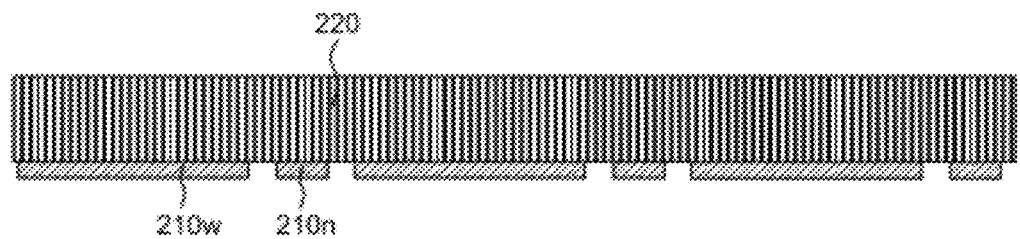
FIGS. 17A-17I are schematic cross-sectional views of a portion of a medical device in accordance with yet another embodiment of the invention and illustrate a method of forming and operating a medical device, in accordance with an embodiment of the invention.
Figure 17B:
Figure 17C:
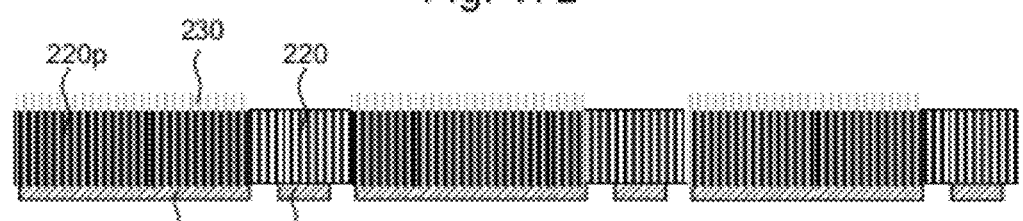
Figure 17D:
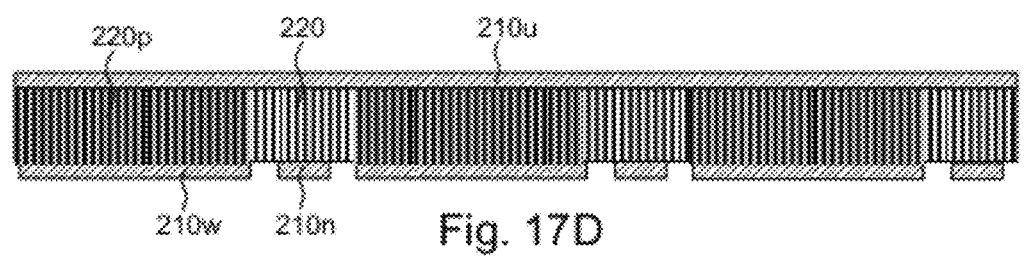
Figure 17E:
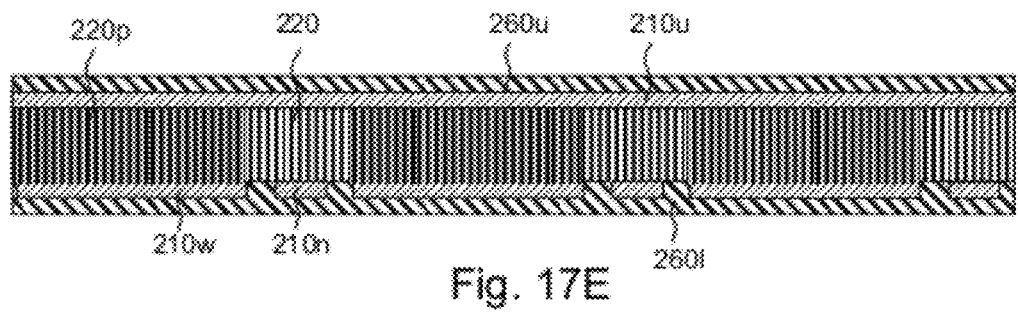
Figure 17F:
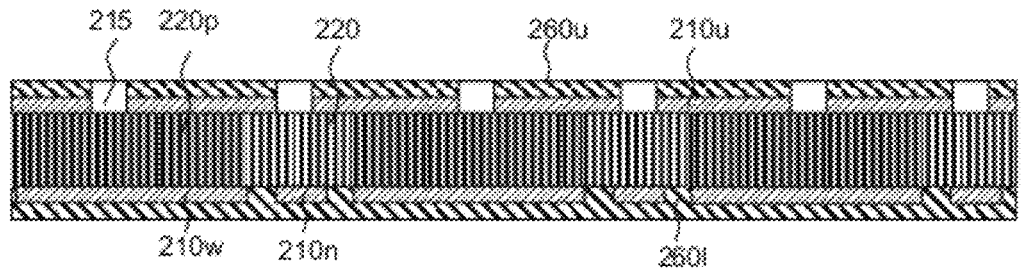
Figure 17G:
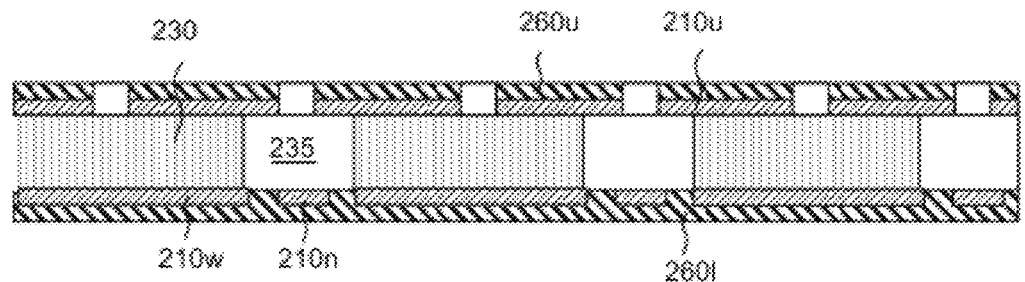
Figure 17H:
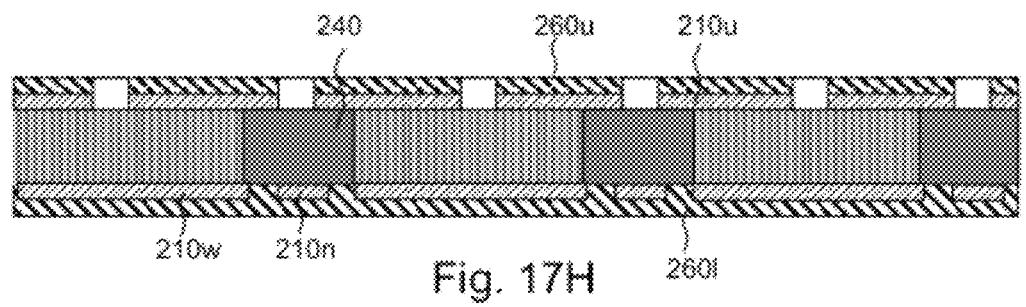
Figure 17I:
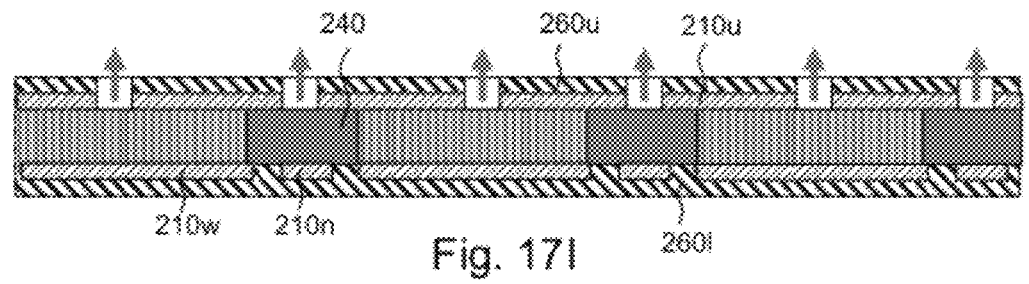

First, a metallic layer (e.g., a gold layer) having narrow metallic stripes 210n and wide metallic stripes 210w is deposited on one side of a porous membrane 220 (e.g., a track-etched polycarbonate membrane) as shown in FIG. 17A. This is followed by electropolymerization of conductive polymer (e.g., polypyrrole doped with a relatively mobile anion) within the pores at the wide stripes 210w, creating regions 220p in which the membrane 220 contains conductive polymer fibers. The top portion of the membrane 220 is then removed, for example, using chloroform as described in A. S. Lee et al., "Electroactive Polymer Actuation at the Nanoscale," *Sixth IEEE Conference on Nanotechnology*, 2006. *IEEE-NANO* 2006, Volume 2, 818-821, exposing the tips of the conductive polymer fibers 230 as shown in FIG. 17C. An upper metallic layer 210u (e.g., a gold layer) is then deposited on the membrane 220, encasing the tips of the conductive polymer fibers to produce the structure shown in FIG. 17D. An upper layer 260u and a lower layer 260l of polymeric material (e.g., polyurethane) is then deposited on the gold layers to insulate and support the same as shown in FIG. 17E. Holes 215 are formed in the upper surface as shown in FIG. 17F, followed by removal of the porous membrane material 220 from the interior of the device, leaving a reservoir 235 that is spanned by the conductive polymer fibers 230 as shown in FIG. 17G. The reservoir is then filled with a therapeutic agent 240 as shown in FIG. 17H. Upon delivery to a patient, the rate of therapeutic agent release from the device can be commenced/increased by reducing the conductive polymer 230 (e.g., by applying a suitable potential between the narrow stripes 210n and wide stripes 210w), which shrinks the fibers 230, drawing the opposing walls together and causing the reservoir to shrink and forcing the therapeutic agent 240 from the device as seen in FIG. 17I.

In certain embodiments of the invention, combinations of the preceding strategies are employed. For example, medical devices may be provided which have the following: (a) at least one first conductive polymer electrode is positioned such that, when the conductive polymer contracts (upon conductive polymer oxidation or reduction), the mouth of at least one reservoir is enlarged and (b) at least one second conductive polymer electrode that is positioned within at least one reservoir such that, when the conductive polymer swells (upon conductive polymer oxidation or reduction), the volume of the reservoir is reduced.

Figure 18A:
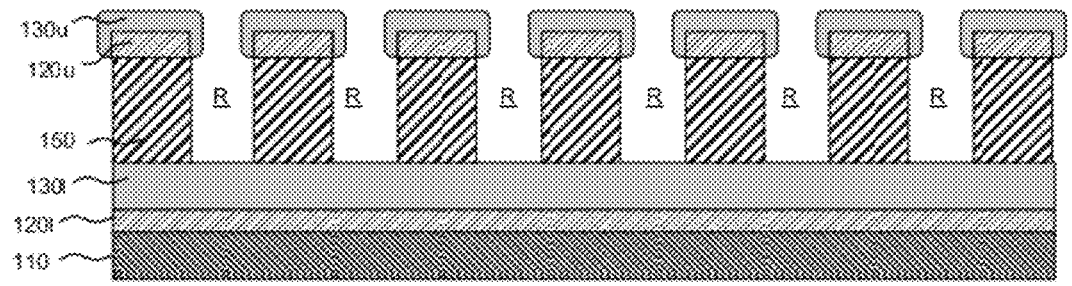
FIG. 18A is a schematic cross-sectional view of a portion of a medical device in accordance with an embodiment of the invention.
Figure 18B:
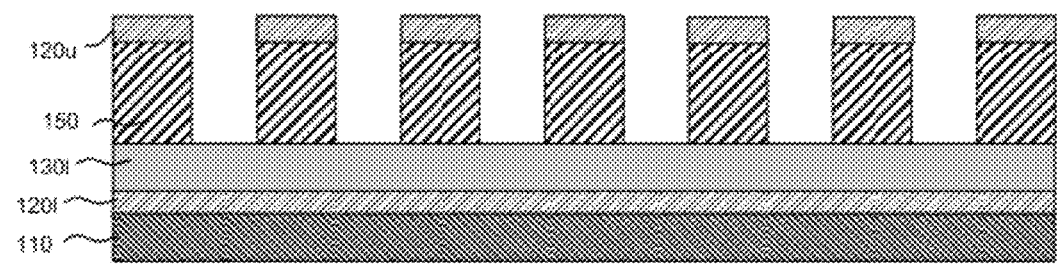
FIG. 18B is a schematic cross-section illustrating the structure of FIG. 18A, prior to the formation of conductive polymer electrodes.

One example of such a device is illustrated in FIG. 18A, which is a schematic cross-sectional view of a portion of a medical device surface in accordance with the invention (e.g., a portion of a balloon, etc.), prior to loading the device with a therapeutic-agent-containing material. FIG. 18A includes a substrate 110, a lower conductive layer 120*l* (e.g., a metal), a lower conductive polymer electrode 130*l*, a layer of depression-forming material 150 (formed here from an electrically insulating material such as a non-conductive polymer), an upper conductive layer 120*u* on top of depression-forming layer 150, and an upper conductive polymer electrode 130*u* formed on the upper conductive layer 120*u*. The structure may be formed, for example, by depositing the lower layer of conductive material 120*l* over the substrate, followed by an electropolymerization process to produce the lower conductive polymer electrode 130*l*. A layer of depression-forming material 150 and a layer of conductive material are deposited over the lower conductive polymer electrode 130*l*, followed by masking and etching to form a structure like that of FIG. 18B. Then, an electropolymerization process is conducted to produce conductive polymer electrode 130*u* as shown in FIG. 18A.

Of course numerous variations on the preceding are possible. For example, if there is good etching selectivity between the conductive polymer material and the depression-forming material, etching of the depression-forming material may be conducted after formation of the conductive polymer electrode 130*u*, that is, a structure like that of FIG. 18C may be etched to produce a structure like that of FIG. 18A.

Figure 18C:
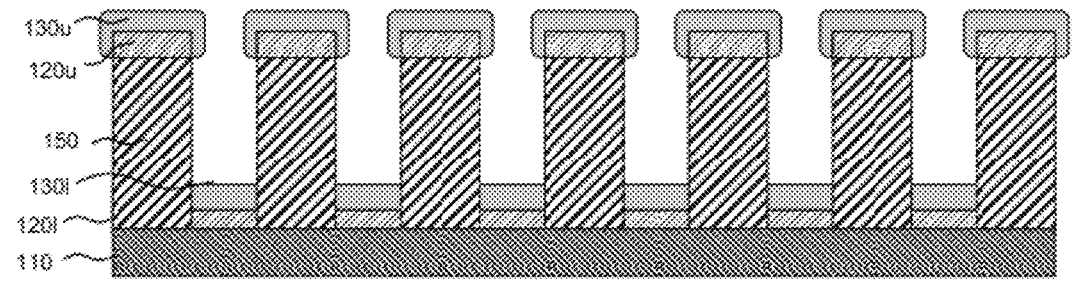
FIG. 18C is a schematic cross-sectional view of a portion of a medical device in accordance with another embodiment of the invention.
Figure 18D:
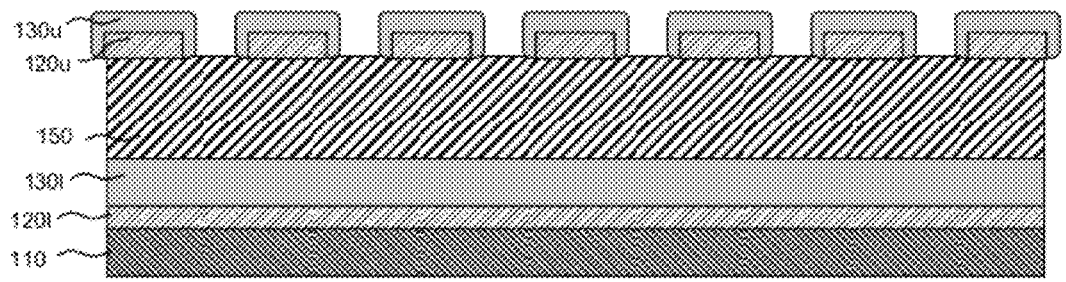
FIG. 18D is a schematic cross-section illustrating the structure of FIG. 18C, prior to etching of reservoirs in the depression-forming material 150 of FIG. 18C.

As another example, rather than depositing the depression-forming material over the lower conductive polymer electrode, the layer of depression-forming material 150 may be formed and patterned on the substrate 110 as shown in FIG. 18C. This may, for example, allow for the possibility of forming the upper conductive layer 120*u* and lower conductive layer 120*l* in a single deposition step (assuming conductive material is not deposited on the walls of the depression-forming material 150, which could provide an electrical short between the upper conductive layer 120*u* and lower conductive layer 120*l*, which result may be avoided by undercutting the walls of the layer 150). This step could then be followed by the formation of the upper conductive polymer electrode 130*u* and lower conductive polymer electrode 130*l* in a single electropolymerization step.

In device structures like those of FIGS. 18A and 18C, the upper conductive polymer electrode 130*u* can act as a counter-electrode for the lower conductive polymer electrode 130*l* during operation, and vice versa.

Figure 19A:
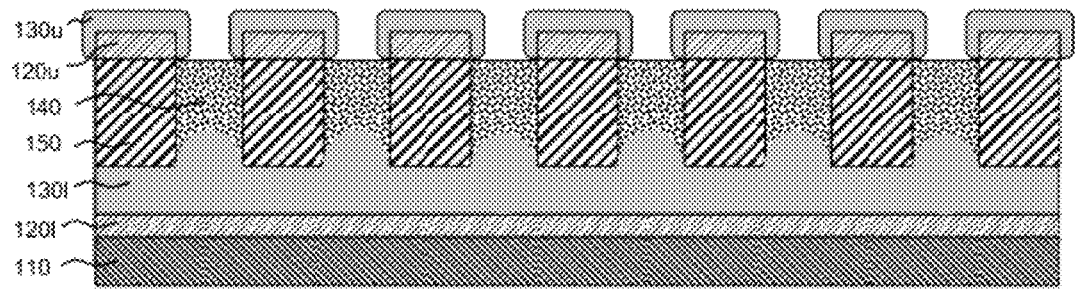
FIG. 19A is a schematic cross-sectional view of the device of FIG. 18A after biasing the upper and lower conductive polymer electrodes such that the upper conductive polymer electrode is contracted and the lower conductive polymer electrode is expanded and after loading the reservoirs with a therapeutic agent. The cross-section of FIG. 19A is taken along line A-A of the schematic top view of FIG. 19B.
Figure 19B:
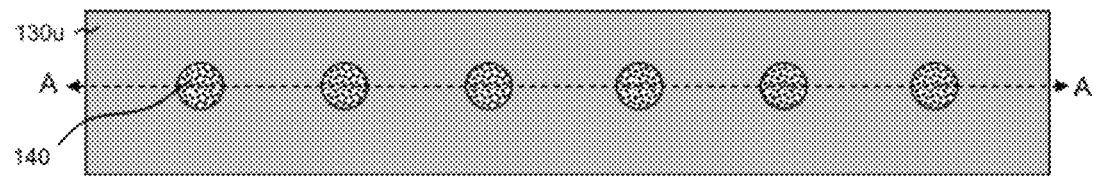

Turning now to FIG. 19A, in the presence of an electrolyte (not shown), the electrodes of a structure like that of FIG. 18A may be biased such that the lower conductive polymer electrode 130*l* is in a swollen state and the upper conductive polymer electrode 130*u* is in a contracted state. For instance, the conductive polymer electrodes 130*l*, 130*u* of FIG. 19A can be formed in the presence of a large (substantially immobile) anion. Assuming the electrodes are contacted with a suitable electrolyte, biasing one electrode (e.g., the upper conductive polymer electrode 130*u*) such that the polypyrrole is oxidized will place that electrode in a contracted state, whereas biasing the other electrode (e.g., the lower conductive polymer electrode 130*l*) such that the electrode is reduced will place that electrode in a swollen state (e.g., due to an influx of charge balancing cations from the electrolyte). In the configuration shown in FIG. 19A, the reservoirs are open to the exterior of the device and can be loaded with a therapeutic-agent-containing material 140. This may be more readily seen from FIG. 19B, which is a schematic top view of FIG. 19A. (FIG. 19A represents the cross-section taken along line A-A of FIG. 19B.)

Figure 20A:
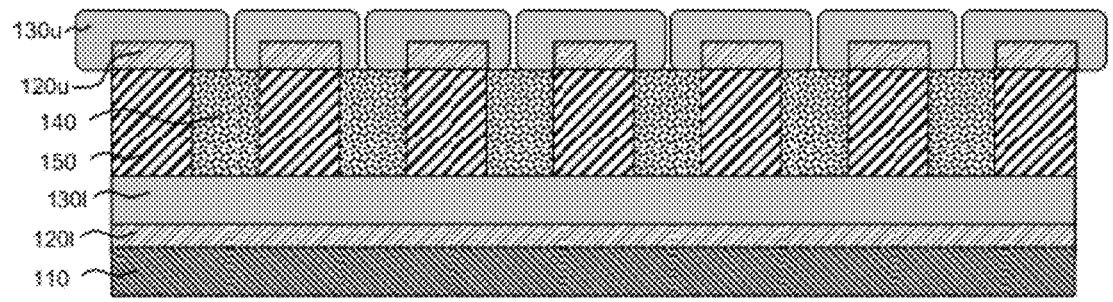
FIG. 20A is a schematic cross-sectional view of the device of FIG. 19A after biasing the upper and lower conductive polymer electrodes such that the upper polymer electrode is expanded the lower conductive polymer electrode is contracted. The cross-section of FIG. 20A is taken along line A-A of the schematic top view of FIG. 20B.
Figure 20B:
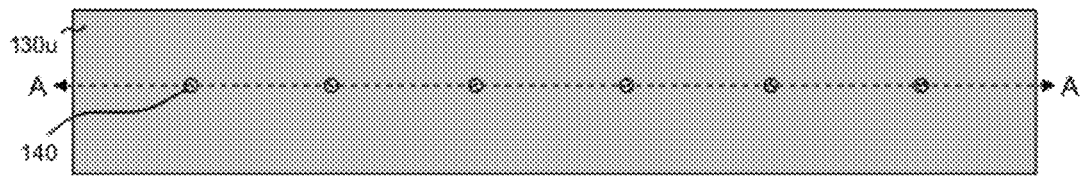

After loading the reservoirs, the electrodes can be biased such that the lower conductive polymer electrode 130*l* is in a contracted state and the upper conductive polymer electrode 130*u* is in a swollen state as shown in FIG. 20A. For example, biasing the lower conductive polymer electrode 130*l* such that the polypyrrole is oxidized will place that electrode in a contracted state (e.g., due to expulsion of cations), whereas biasing the upper conductive polymer electrode 130*u* such that the electrode is reduced will place that electrode in an expanded state (e.g., due to an influx of cations). In the configuration shown in FIG. 20A, the reservoirs are substantially closed to the exterior of the device as seen, for example, from the schematic top view of FIG. 20B. (FIG. 20A is a cross-section taken along line A-A of FIG. 20B.)

By again reversing the bias of the electrodes 130*l*, 130*u* in vivo, the structure can be reverted to that of FIG. 19A, opening the reservoirs by shrinking the upper conductive polymer electrode 130*u*. Moreover, the lower conductive polymer electrode 130*l* is swollen. These effects promote the expulsion of the therapeutic-agent-containing material 140.

In addition, as indicated above, conductive polymer electrodes have been developed which are not only observed to swell but also to become more hydrophilic upon reduction. Conversely, these electrodes have been observed to shrink and become more hydrophobic upon oxidation. By employing such electrodes in combination with a hydrophobic therapeutic-agent-containing material 140 (e.g., paclitaxel or an olimus family drug such as everolimus or 6-mercaptopurine dissolved in a hydrophobic liquid), the therapeutic-agent-containing material 140 is urged from the reservoirs not only as a result of the swelling of the lower conductive polymer electrode 130*l*, but also as a result of hydrophilic-hydrophobic repulsion that occurs upon switching of the lower conductive polymer electrode 130*l* from a hydrophobic to a hydrophilic state.

Figure 21A:
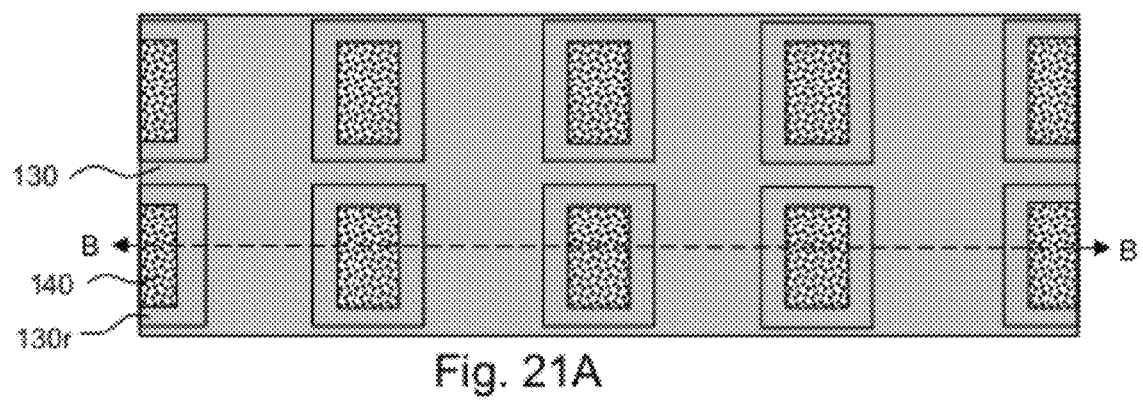
FIG. 21A is a schematic top view of a portion of a surface of a medical device in accordance with an embodiment of the invention.
Figure 21B:
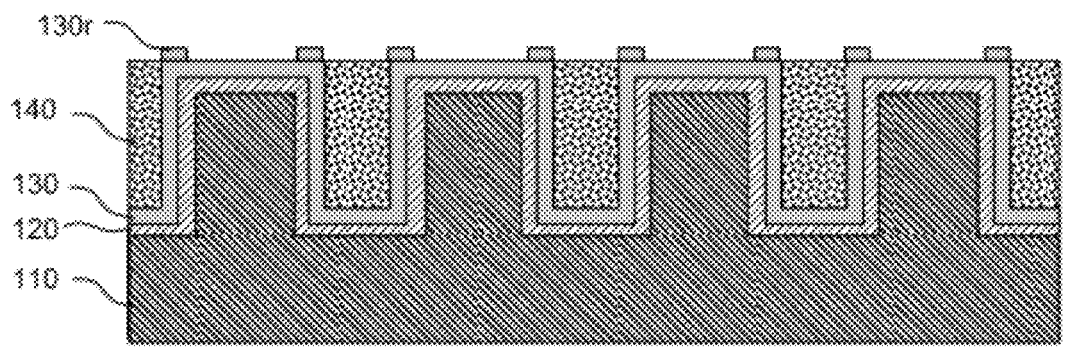
FIG. 21B is a schematic cross-section taken along line B-B of FIG. 21A.

In certain embodiments of the invention, the surface topography of the device may be used to assist with therapeutic agent delivery. For example, FIG. 21A is a schematic top view of a portion of a surface of a medical device in accordance with the invention. FIG. 21B is a cross-section taken along line B-B in FIG. 21A. FIGS. 21A-21B are analogous to FIGS. 1A-1B in that they include a substrate 110, within which are formed various depressions. Disposed over the substrate 110 is a thin metallic layer 120 upon which is provided a conductive polymer electrode 130 (e.g., an electrodeposited polypyrrole layer which is doped with a suitable anion). The depressions of the structure are filled with a therapeutic-agent-containing material 140. Unlike FIGS. 1A-1B, however, the depressions are pores (i.e., rectangular pores) rather than trenches. Moreover, rim of each pore is provided with a raised ring 130*r* (i.e., a rectangular ring) of material (e.g., a ring of conductive polymer material or another flexible material).

The device illustrated in FIGS. 21A-21B may represent, for example, a portion of the balloon of a balloon catheter in accordance with the invention. In such an embodiment, the raised ring 130*r* can act as a seal, so long as the balloon is expanded against the vessel wall. Moreover, upon retraction of the balloon, the raised ring 130r may promote the formation of a negative pressure within the reservoir (much like the retraction of a previously compressed toilet plunger creates a negative pressure), assisting with therapeutic agent delivery.

As indicated above, medical devices in accordance with the present invention are therapeutic agent delivery devices. "Therapeutic agents," drugs," "bioactive agents, "pharmaceuticals," "pharmaceutically active agents", and other related terms may be used interchangeably herein and include genetic and non-genetic therapeutic agents.

Therapeutic agents may be used singly or in combination. In the preceding embodiments, the medical devices of the present invention are described as delivering a single therapeutic agent. In other embodiments, however, multiple types of therapeutic agent are delivered. For example, in embodiments pertaining to the treatment of restenosis (e.g., where the device is a drug-delivering medical balloon) it may be desirable to deliver a vasodilating agent prior to the delivery of an antirestenotic agent. Such agents may be released, for instance, as a mixture of they may be released from different reservoirs on the medical device surface. As one example, alternating reservoirs (trenches) of the device of FIGS. 14A-B may be supplied with differing therapeutic agents. As another example, alternating reservoirs (pores) of the device of FIGS. 11A-B may be supplied with differing therapeutic agents (e.g., in a "checkerboard" fashion).

A wide range of therapeutic agent loadings can be used in conjunction with the devices of the present invention, with the pharmaceutically effective amount being readily determined by those of ordinary skill in the art and ultimately depending, for example, upon the condition to be treated, the nature of the therapeutic agent itself, the tissue to which the device is introduced, the duration of the exposure of the therapeutic agent to the tissue, and so forth.

In those specific embodiments of the invention where the medical device is configured to release paclitaxel for the treatment of restenosis, the amount of paclitaxel in the device may vary widely, for example, ranging from 0.01 to 0.025 to 0.05 to 0.1 to 0.25 to 0.5 to 1 to 2.5 to 5 micrograms per $mm^2$ of device surface (e.g., per $mm^2$ of balloon surface). In another specific example, where the medical device of the invention is configured to release everolimus for the treatment of restenosis, the amount of everolimus on the device may vary widely, for example, ranging from 0.025 to 0.05 to 0.1 to 0.25 to 0.5 to 1 to 2.5 to 5 to 10 micrograms per $mm^2$ of device surface (e.g., per $mm^2$ of balloon surface). In yet another specific example, where the medical device of the invention is configured to release 6-mercaptopurine for the treatment of restenosis, the amount of 6-mercaptopurine on the device may vary widely, for example, ranging from 1 to 2.5 to 5 to 10 to 25 to 50 to 100 to 250 micrograms per $mm^2$ of device surface (e.g., balloon surface).

Therapeutic agents include non-ionic therapeutic agents, cationic therapeutic agents and anionic therapeutic agents. Such therapeutic agents may be disposed in the reservoirs of the invention. For example such therapeutic agents may be disposed in the reservoirs in pure form or admixed or covalently bound to an additional compound within the reservoirs. Examples of such additional compounds include compounds having one or more of the following characteristics: compounds which increase the solubility of the therapeutic agent and compounds which increase the uptake of the therapeutic agent by adjacent tissue. One example of such a material is iopromide (an iodine-based contrast medium) which is known to significantly increase the solubility of antirestenotic drugs in saline (specifically, paclitaxel). Iopromide is also known to adhere to vessel walls for several seconds after exposure and thus may act as a temporary in vivo matrix for antirestenotic drugs such as paclitaxel. See, e.g., B. Scheller et al., Journal of the American College of Cardiology, 42(8), 2003, 1415-1420. Other examples of such additional compounds include compounds which inhibiting proteins that are responsible for pumping therapeutic agents out of cells after uptake, thereby increasing the concentration of the therapeutic agents within the cells. For example, P-glycoprotein (P-gp) is one of the most important transport proteins implicated in multidrug resistance in neoplastic tissues. In cancer tissue with high expression of this protein, P-gp functions as a drug export pump that decreases intracellular concentrations of numerous chemotherapeutic agents, including paclitaxel. Paclitaxel, as well as many other chemotherapeutic agents, are used in blocking smooth muscle cell proliferation responsible for restenosis. Thus, inhibiting (P-gp) would as well be effective in obtaining a higher intracellular dose in vessel walls treated with devices in accordance with the invention (e.g, a drug eluting balloon). Thus in certain embodiments a P-glycoprotein inhibitor is co-released with an anti-restenotic agent. Examples of P-glycoprotein inhibitors include, for example, cyclosporin D and its analogs (e.g, valspodar, etc.).

In those embodiments where the therapeutic agents are covalently bound to an additional compound, the bond may be selected may be such that it is readily broken at acidic pH (which is produced at the anode at suitable anodic bias) or alkaline pH (which is produced at the cathode at suitable anodic bias). Specific examples of such materials include (a) acid sensitive polyethylene glycol (PEG) conjugates in which paclitaxel is attached to PEG (which acts as a solubilizing agent) via a hydrazone linker (see, e.g., K. Ulbrich, "Polymeric anticancer drugs with pH-controlled activation," Advanced Drug Delivery Reviews, 56 (2004) 1023-1050 and references cited therein) and (b) paclitaxel 2'-N-methylpyridinium mesylate (PNMM),

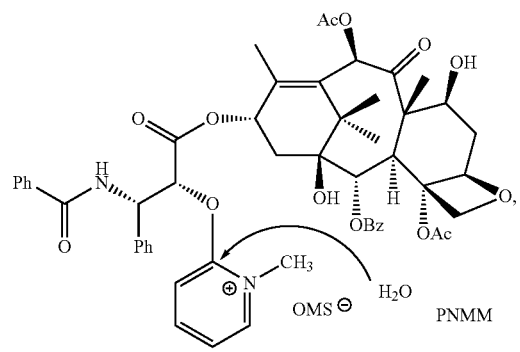

in which the hydrolysis of the bond attaching the paclitaxel and N-methylpyridine entity (which acts as a solubilizing agent) has been reported to exhibit base catalysis (see, e.g., Jaber G. Qasem et al, AAPS PharmSciTech 2003, 4(2) Article 21). Note that substitution of one or more ring hydrogens of the N-methylpyridinium moiety of the PNMM with iodine may render the paclitaxel conjugate radiopaque.

In those embodiments where the therapeutic agent is an anionic therapeutic agent, the therapeutic agent may be disposed in the conductive polymer electrodes of the invention (e.g., co-deposited with polypyrrole or another conductive polymer in an electropolymerization process). Note that in such cases, the anionic therapeutic agent is typically not covalently bound to the conductive polymer that is formed.

Exemplary therapeutic agents for use in conjunction with the present invention may be selected, for example, from the following, among others: (a) anti-thrombotic agents such as heparin, heparin derivatives, urokinase, clopidogrel, and PPack (dextrophenylalanine proline arginine chloromethylketone); (b) anti-inflammatory agents such as dexamethasone, prednisolone, corticosterone, budesonide, estrogen, sulfasalazine and mesalamine; (c) antineoplastic/antiproliferative/anti-miotic agents such as paclitaxel, 5-fluorouracil, cisplatin, vinblastine, vincristine, epothilones, endostatin, angiostatin, angiopeptin, monoclonal antibodies capable of blocking smooth muscle cell proliferation, and thymidine kinase inhibitors; (d) anesthetic agents such as lidocaine, bupivacaine and ropivacaine; (e) anti-coagulants such as D-Phe-Pro-Arg chloromethyl ketone, an RGD peptide-containing compound, heparin, hirudin, antithrombin compounds, platelet receptor antagonists, anti-thrombin antibodies, anti-platelet receptor antibodies, aspirin, prostaglandin inhibitors, platelet inhibitors and tick antiplatelet peptides; (f) vascular cell growth promoters such as growth factors, transcriptional activators, and translational promotors; (g) vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; (h) protein kinase and tyrosine kinase inhibitors (e.g., tyrphostins, genistein, quinoxalines); (i) prostacyclin analogs; (j) cholesterol-lowering agents; (k) angiopoietins; (l) antimicrobial agents such as triclosan, cephalosporins, aminoglycosides and nitrofurantoin; (m) cytotoxic agents, cytostatic agents and cell proliferation affectors; (n) vasodilating agents; (o) agents that interfere with endogenous vasoactive mechanisms; (p) inhibitors of leukocyte recruitment, such as monoclonal antibodies; (q) cytokines; (r) hormones; (s) inhibitors of HSP 90 protein (i.e., Heat Shock Protein, which is a molecular chaperone or housekeeping protein and is needed for the stability and function of other client proteins/signal transduction proteins responsible for growth and survival of cells) including geldanamycin, (t) smooth muscle relaxants such as alpha receptor antagonists (e.g., doxazosin, tamsulosin, terazosin, prazosin and alfuzosin), calcium channel blockers (e.g., verapimil, diltiazem, nifedipine, nicardipine, nimodipine and bepridil), beta receptor agonists (e.g., dobutamine and salmeterol), beta receptor antagonists (e.g., atenolol, metaprolol and butoxamine), angiotensin-II receptor antagonists (e.g., losartan, valsartan, irbesartan, candesartan, eprosartan and telmisartan), and antispasmodic/anticholinergic drugs (e.g., oxybutynin chloride, flavoxate, tolterodine, hyoscyamine sulfate, diclomine), (u) bARKct inhibitors, (v) phospholamban inhibitors, (w) Serca 2 gene/protein, (x) immune response modifiers including aminoquizolines, for instance, imidazoquinolines such as resiquimod and imiquimod, (y) human apolioproteins (e.g., AI, AII, AIII, AIV, AV, etc.), (z) selective estrogen receptor modulators (SERMs) such as raloxifene, lasofoxifene, arzoxifene, miproxifene, ospemifene, PKS 3741, MF 101 and SR 16234, (aa) PPAR agonists, including PPAR-alpha, gamma and delta agonists, such as rosiglitazone, pioglitazone, netoglitazone, fenofibrate, bexaotene, metaglidasen, rivoglitazone and tesaglitazar, (bb) prostaglandin E agonists, including PGE2 agonists, such as alprostadil or ONO 8815Ly, (cc) thrombin receptor activating peptide (TRAP), (dd) vasopeptidase inhibitors including benazepril, fosinopril, lisinopril, quinapril, ramipril, imidapril, delapril, moexipril and spirapril, (ee) thymosin beta 4, (ff) phospholipids including phosphorylcholine, phosphatidylinositol and phosphatidylcholine, and (gg) VLA-4 antagonists and VCAM-1 antagonists.

Numerous therapeutic agents, not necessarily exclusive of those listed above, have been identified as candidates for vascular treatment regimens, for example, as agents targeting restenosis (antirestenotics). Such agents are useful for the practice of the present invention and may be selected, for example, from one or more of the following: (a) Ca-channel blockers including benzothiazapines such as diltiazem and clentiazem, dihydropyridines such as nifedipine, amlodipine and nicardapine, and phenylalkylamines such as verapamil, (b) serotonin pathway modulators including: 5-HT antagonists such as ketanserin and naftidrofuryl, as well as 5-HT uptake inhibitors such as fluoxetine, (c) cyclic nucleotide pathway agents including phosphodiesterase inhibitors such as cilostazole and dipyridamole, adenylate/Guanylate cyclase stimulants such as forskolin, as well as adenosine analogs, (d) catecholamine modulators including α-antagonists such as prazosin and bunazosine, β-antagonists such as propranolol and α/β-antagonists such as labetalol and carvedilol, (e) endothelin receptor antagonists such as bosentan, sitaxsentan sodium, atrasentan, endonentan, (f) nitric oxide donors/releasing molecules including organic nitrates/nitrites such as nitroglycerin, isosorbide dinitrate and amyl nitrite, inorganic nitroso compounds such as sodium nitroprusside, sydnonimines such as molsidomine and linsidomine, nonoates such as diazenium diolates and NO adducts of alkanediamines, S-nitroso compounds including low molecular weight compounds (e.g., S-nitroso derivatives of captopril, glutathione and N-acetyl penicillamine) and high molecular weight compounds (e.g., S-nitroso derivatives of proteins, peptides, oligosaccharides, polysaccharides, synthetic polymers/oligomers and natural polymers/oligomers), as well as C-nitroso-compounds, O-nitroso-compounds, N-nitroso-compounds and L-arginine, (g) Angiotensin Converting Enzyme (ACE) inhibitors such as cilazapril, fosinopril and enalapril, (h) ATII-receptor antagonists such as saralasin and losartin, (i) platelet adhesion inhibitors such as albumin and polyethylene oxide, (j) platelet aggregation inhibitors including cilostazole, aspirin and thienopyridine (ticlopidine, clopidogrel) and GP IIb/IIIa inhibitors such as abciximab, epitifibatide and tirofiban, (k) coagulation pathway modulators including heparinoids such as heparin, low molecular weight heparin, dextran sulfate and β-cyclodextrin tetradecasulfate, thrombin inhibitors such as hirudin, hirulog, PPACK(D-phe-L-propyl-L-arg-chloromethylketone) and argatroban, FXa inhibitors such as antistatin and TAP (tick anticoagulant peptide), Vitamin K inhibitors such as warfarin, as well as activated protein C, (l) cyclooxygenase pathway inhibitors such as aspirin, ibuprofen, flurbiprofen, indomethacin and sulfinpyrazone, (m) natural and synthetic corticosteroids such as dexamethasone, prednisolone, methprednisolone and hydrocortisone, (n) lipoxygenase pathway inhibitors such as nordihydroguairetic acid and caffeic acid, (o) leukotriene receptor antagonists, (p) antagonists of E- and P-selectins, (q) inhibitors of VCAM-1 and ICAM-1 interactions, (r) prostaglandins and analogs thereof including prostaglandins such as PGE1 and PGI2 and prostacyclin analogs such as ciprostene, epoprostenol, carbacyclin, iloprost and beraprost, (s) macrophage activation preventers including bisphosphonates, (t) HMG-CoA reductase inhibitors such as lovastatin, pravastatin, atorvastatin, fluvastatin, simvastatin and cerivastatin, (u) fish oils and omega-3-fatty acids, (v) free-radical scavengers/antioxidants such as probucol, vitamins C and E, ebselen, trans-retinoic acid, SOD (orgotein) and SOD mimics, verteporfin, rostaporfin, AGI 1067, and M 40419, (w) agents affecting various growth factors including FGF pathway agents such as bFGF antibodies and chimeric fusion proteins, PDGF receptor antagonists such as trapidil, IGF pathway agents including somatostatin analogs such as angiopeptin and ocreotide, TGF-β pathway agents such as polyanionic agents (heparin, fucoidin), decorin, and TGF-β antibodies, EGF pathway agents such as EGF antibodies, receptor antagonists and chimeric fusion proteins, TNF-α pathway agents such as thalidomide and analogs thereof, Thromboxane A2 (TXA2) pathway modulators such as sulotroban, vapiprost, dazoxiben and ridogrel, as well as protein tyrosine kinase inhibitors such as tyrphostin, genistein and quinoxaline derivatives, (x) matrix metalloprotease (MMP) pathway inhibitors such as marimastat, ilomastat, metastat, batimastat, pentosan polysulfate, rebimastat, incyclinide, apratastat, PG 116800, RO 1130830 or ABT 518, (y) cell motility inhibitors such as cytochalasin B, (z) antiproliferative/antineoplastic agents including antimetabolites such as purine antagonists/ analogs (e.g., 6-mercaptopurine and pro-drugs of 6-mercaptopurine such as azathioprine or cladribine, which is a chlorinated purine nucleoside analog), pyrimidine analogs (e.g., cytarabine and 5-fluorouracil) and methotrexate, nitrogen mustards, alkyl sulfonates, ethylenimines, antibiotics (e.g., daunorubicin, doxorubicin), nitrosoureas, cisplatin, agents affecting microtubule dynamics (e.g., vinblastine, vincristine, colchicine, Epo D, paclitaxel and epothilone), caspase activators, proteasome inhibitors, angiogenesis inhibitors (e.g., endostatin, angiostatin and squalamine), olimus family drugs (e.g., sirolimus, everolimus, tacrolimus, zotarolimus, etc.), cerivastatin, flavopiridol and suramin, (aa) matrix deposition/organization pathway inhibitors such as halofuginone or other quinazolinone derivatives, pirfenidone and tranilast, (bb) endothelialization facilitators such as VEGF and RGD peptide, (cc) blood rheology modulators such as pentoxifylline and (dd) glucose cross-link breakers such as alagebrium chloride (ALT-711).

Preferred non-genetic therapeutic agents include taxanes such as paclitaxel (including particulate forms thereof, for instance, protein-bound paclitaxel particles such as albumin-bound paclitaxel nanoparticles, e.g., ABRAXANE), olimus family drugs such as sirolimus, everolimus, tacrolimus and zotarolimus, Epo D, dexamethasone, purine antagonists/analogs such as 6-mercaptopurine, estradiol, halofuginone, cilostazole, geldanamycin, alagebrium chloride (ALT-711), ABT-578 (Abbott Laboratories), trapidil, liprostin, Actinomcin D, Resten-NG, Ap-17, abciximab, clopidogrel, Ridogrel, beta-blockers, bARKct inhibitors, phospholamban inhibitors, Serca 2 gene/protein, imiquimod, human apolioproteins (e.g., AI-AV), growth factors (e.g., VEGF-2), as well derivatives and prodrugs of the forgoing, among others.

Numerous additional therapeutic agents useful for the practice of the present invention are also disclosed in U.S. Pat. No. 5,733,925 to Kunz, the entire disclosure of which is incorporated by reference.

Although various embodiments are specifically illustrated and described herein, it will be appreciated that modifications and variations of the present invention are covered by the above teachings and are within the purview of the appended claims without departing from the spirit and intended scope of the invention.

The invention claimed is:

1. A medical device comprising: a reservoir having an internal surface, a therapeutic-agent-containing material that comprises a therapeutic agent disposed within the reservoir, and a first electrode comprising a first conductive polymer that defines at least a portion of the internal surface of the reservoir, wherein a rate of release of the therapeutic agent from the reservoir begins or is increased upon the application of a potential that is sufficient to change the oxidation state of the first conductive polymer, wherein the conductive polymer reversibly swells or shrinks upon the change in oxidation state,
   (a) wherein the first conductive polymer defines at least a portion of a surface of walls of the reservoir and wherein the change in oxidation state swells the first conductive polymer, reducing the volume of the reservoir and expelling the therapeutic-agent-containing material such that the rate of release of the therapeutic agent from the reservoir begins or is increased or
   (b) wherein the first conductive polymer connects two opposing walls of material which form said reservoir and wherein the change in oxidation state shrinks the first conductive polymer such that the walls are drawn together, reducing the volume of the reservoir and expelling the therapeutic-agent-containing material such that the rate of release of the therapeutic agent from the reservoir begins or is increased.

2. The medical device of claim 1, further comprising a second electrode.

3. The medical device of claim 1, further comprising a power source that is adapted to apply said potential.

4. The medical device of claim 1, wherein said medical device is configured for electrical connection with an external power supply.

5. The medical device of claim 1, wherein said device is an elongated device that comprises an insulated electrical conductor that (a) extends proximally from the first electrode and (b) is in electrical contact with the first electrode.

6. A medical device comprising: a reservoir having an internal surface, a therapeutic-agent-containing material that comprises a therapeutic agent disposed within the reservoir, and a first electrode comprising a first conductive polymer that defines at least a portion of the internal surface of the reservoir, wherein a rate of release of the therapeutic agent from the reservoir begins or is increased upon the application of a potential that is sufficient to change the oxidation state of the first conductive polymer, wherein the conductive polymer reversibly swells or shrinks upon the change in oxidation state, wherein said reservoir is capped with an ion permeable barrier layer.

7. The medical device of claim 1, wherein the first conductive polymer defines at least a portion of the surface of walls of the reservoir, wherein the change in oxidation state swells the first conductive polymer, reducing the volume of the reservoir and expelling the therapeutic-agent-containing material such that the rate of release of the therapeutic agent from the reservoir begins or is increased, and wherein the reservoir is formed in a depression that is formed in a substrate material or in a material that is disposed over a substrate material.

8. The medical device of claim 7, wherein the depression is in the form of a trench or a pore.

9. The medical device of claim 1, wherein the first conductive polymer defines at least a portion of the surface of walls of the reservoir, wherein the change in oxidation state swells the first conductive polymer, reducing the volume of the reservoir and expelling the therapeutic-agent-containing material such that the rate of release of the therapeutic agent from the reservoir begins or is increased.

10. The medical device of claim 9, wherein the change in oxidation state switches the first conductive polymer to a more hydrophilic state.

11. The medical device of claim 9, wherein the reservoir is at least partially formed within the first conductive polymer.

12. The medical device of claim 9, wherein the first conductive polymer is in the form of a layer that lines at least a portion of a depression.

13. The medical device of claim 1, wherein first conductive polymer connects two opposing walls of material which form said reservoir and wherein the change in oxidation state shrinks the first conductive polymer such that the walls are drawn together, reducing the volume of the reservoir and expelling the therapeutic-agent-containing material such that the rate of release of the therapeutic agent from the reservoir begins or is increased.

14. The medical device of claim 1, further comprising a second electrode that comprises a second conductive polymer.

15. The medical device of claim 14, wherein the rate of release of the therapeutic agent from the reservoir begins or is increased upon swelling of the first conductive polymer and upon shrinkage of the second conductive polymer.

16. A medical device comprising: (a) a reservoir having an internal surface, (b) a therapeutic-agent-containing material that comprises a therapeutic agent disposed within the reservoir, (c) a first electrode comprising a first conductive polymer, and (d) a second electrode that comprises a second conductive polymer, wherein the first conductive polymer defines at least a portion of the surface of walls of the reservoir and wherein the second conductive polymer defines at least a portion of the surface of the mouth of the reservoir, and wherein a rate of release of the therapeutic agent from the reservoir begins or is increased upon the application of a potential that is sufficient to change the oxidation state of the first and second conductive polymers such that the first conductive polymer swells and the second conductive polymer shrinks.

17. The medical device of claim 1, wherein the medical device is an insertable or implantable device selected from a balloon catheter and a tissue regeneration device.

18. The medical device of claim 1, wherein the medical device is an insertable device comprising an elongate shaft and a radially expandable member.

19. The medical device of claim 18, wherein the radially expandable member is a balloon.

20. The medical device of claim 1, wherein the therapeutic agent is an uncharged therapeutic agent.

21. The medical device of claim 1, wherein the therapeutic agent is selected from an antirestenotic agent, a growth factor and a growth factor stimulating agent.

22. The medical device of claim 1, wherein the therapeutic agent is selected from paclitaxel, everolimus and 6-mercaptopurine.

23. The medical device of claim 22, wherein the paclitaxel is admixed with a contrast agent.

24. The medical device of claim 1, wherein the medical device is an insertable device comprising an elongate shaft and a radially expandable member.

25. The medical device of claim 18, wherein the radially expandable member is a balloon.

* * * * *